US012576158B2

(12) United States Patent
Mueller et al.

(10) Patent No.: US 12,576,158 B2
(45) Date of Patent: Mar. 17, 2026

(54) ANTIBODY DRUG CONJUGATES WITH CLEAVABLE LINKERS

(71) Applicant: Heidelberg Pharma Research GmbH, Ladenburg (DE)

(72) Inventors: Christoph Mueller, Ladenburg (DE); Werner Simon, Ladenburg (DE); Susanne Werner-Simon, Ladenburg (DE); Francesca Gallo, Ladenburg (DE); Torsten Hechler, Ladenburg (DE); Michael Kulke, Ladenburg (DE); Andreas Pahl, Ladenburg (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 1150 days.

(21) Appl. No.: 17/613,638

(22) PCT Filed: May 22, 2020

(86) PCT No.: PCT/EP2020/064298

§ 371 (c)(1),
(2) Date: Nov. 23, 2021

(87) PCT Pub. No.: WO2020/234461

PCT Pub. Date: Nov. 26, 2020

(65) Prior Publication Data

US 2023/0173087 A1 Jun. 8, 2023

(30) Foreign Application Priority Data

May 23, 2019 (EP) .................................... 19176278

(51) Int. Cl.
*A61P 35/00* (2006.01)
*A61K 47/68* (2017.01)

(52) U.S. Cl.
CPC ...... *A61K 47/6831* (2017.08); *A61K 47/6849* (2017.08); *A61K 47/6851* (2017.08); *A61K 47/6889* (2017.08); *A61P 35/00* (2018.01)

(58) Field of Classification Search
CPC .................................................. A61K 47/6831
See application file for complete search history.

(56) References Cited

U.S. PATENT DOCUMENTS

| | | | |
|---|---|---|---|
| 11,530,295 | B2 | 12/2022 | Tsubusaki et al. |
| 2021/0030887 | A1 | 2/2021 | Zhu et al. |

FOREIGN PATENT DOCUMENTS

| | | | | |
|---|---|---|---|---|
| WO | 2014/135282 A1 | 9/2014 | | |
| WO | 2015/152182 A1 | 10/2015 | | |
| WO | WO 2016/142049 A1 | 9/2016 | | |
| WO | 2017/149077 A1 | 9/2017 | | |
| WO | WO-2017214024 A1 | * 12/2017 | .......... | A61K 31/357 |
| WO | 2019/034175 A1 | 2/2019 | | |

OTHER PUBLICATIONS

Binz et al., "Engineering novel binding proteins from nonimmunoglobulin domains", Nature Biotechnology, vol. 23, No. 10, Oct. 6, 2005, pp. 1257-1268.
Chalouni et al., "Fate of Antibody-Drug Conjugates in Cancer Cells", Journal of Experimental & Clinical Cancer Research, vol. 37, No. 20, 2018, pp. 1-12.
Jeffery et al., "Design, Synthesis, and in Vitro Evaluation of Dipeptide-Based Antibody Minor Groove Binder Conjugates", J. Med. Chem., vol. 48, No. 5, Feb. 5, 2005, pp. 1344-1358.
Jeffery et al., "Development and Properties of β-Glucuronide Linkers for Monoclonal Antibody-Drug Conjugates", Bioconjugate Chem., vol. 17, No. 3, Jan. 26, 2006, pp. 831-840.
Roberto J Poljak, "Production and structure of diabodies", Structure, vol. 2, No. 12, Dec. 15, 1994, pp. 1121-1123.
Tranoy-Opalinski et al., "β-Glucuronidase-responsive prodrugs for selective cancer chemotherapy: An update", European Journal of Medicinal Chemistry, vol. 74, Jan. 11, 2014, pp. 302-313.
Wang et al., "Three decades of nucleic acid aptamer technologies: Lessons learned, progress and opportunities on aptamer development", Biotechnology Advances, vol. 37, Nov. 5, 2018, pp. 28-50.
Wieland et al., "Amatoxins, Phallotoxins, Phallolysin, and Antamanide: The Biologically Active Components of Poisonous Amanita Mushrooms", Critical Reviews in Biochemistry, Dec. 1978, pp. 185-260.
Japan Patent Office, Office Action in Japanese Patent Application No. 2021-569277 (Jun. 25, 2024).
Israel Patent Office, Notice of Deficiencies in Israeli Patent Application No. 287711 (Jul. 9, 2024).
Japan Patent Office, Office Action in Japanese Patent Application No. 2021-569277 (Dec. 12, 2023).
Office Action issued by the Korean Intellectual Property Office in Korean Patent Application No. 10-2021-7038137 on Jan. 23, 2025, 25 pages (with English translation).
Gillies et al., "Acetals as pH-Sensitive Linkages for Drug Delivery," *Bioconjugate Chem*., 15: 1254-1263 (2004).
European Patent Office, International Search Report for International Patent Application PCT/EP2020/064298 (Aug. 14, 2020).

* cited by examiner

*Primary Examiner* — John S Kenyon
*Assistant Examiner* — Rehana Ismail
(74) *Attorney, Agent, or Firm* — Grüneberg Global IP, PLLC

(57) ABSTRACT

The present invention relates to prodrugs comprising a linker comprising five- or six-membered cyclic acetals and an adjacent specific cleavage site, and to precursor compounds for the synthesis of said prodrugs. In one aspect the present invention relates to antibody-targeted amatoxin conjugates comprising said linkers, to methods for their synthesis, and to the use of said antibody-targeted amatoxin conjugates. In a further aspect, the invention relates to pharmaceutical compositions comprising said conjugates, and to the use of said conjugates or compositions for therapeutic purposes, in particular for tumor therapy and oncology.

22 Claims, 6 Drawing Sheets

| T-D265C | EC 50 [M] |
|---|---|
| 30.2672 | ($7.19 \times 10^{-10}$) |
| 30.2684 | $1.44 \times 10^{-11}$ |
| 30.1699 | $1.25 \times 10^{-11}$ |

| T-D265C | EC 50 [M] |
|---|---|
| 30.2672 | $(1.52 \times 10^{-09})$ |
| 30.2684 | $3.56 \times 10^{-11}$ |
| 30.1699 | $3.31 \times 10^{-11}$ |

| T-D265C | EC 50 [M] |
|---|---|
| 30.2672 | - |
| 30.2684 | $1.69 \times 10^{-10}$ |
| 30.1699 | $2.77 \times 10^{-10}$ |

ANTIBODY DRUG CONJUGATES WITH CLEAVABLE LINKERS

FIELD OF THE INVENTION

The present invention relates to prodrugs comprising a linker comprising five- or six-membered cyclic acetals and an adjacent specific cleavage site, and to precursor compounds for the synthesis of said prodrugs. In one aspect the present invention relates to antibody-targeted amatoxin conjugates comprising said linkers, to methods for their synthesis, and to the use of said antibody-targeted amatoxin conjugates. In a further aspect, the invention relates to pharmaceutical compositions comprising said conjugates, and to the use of said conjugates or compositions for therapeutic purposes, in particular for tumor therapy and oncology.

BACKGROUND

Prodrugs are pharmacologically inactive medications that have to be converted to an active form through biochemical or chemical reactions, such as hydrolysis or phosphorylation. The idea of prodrugs in cancer therapy is to reduce unintended side effects by designing compounds that interact with specific targets. These prodrugs are comprising a target-binding moiety which is linked to the therapeutic or toxic component, often via a linker component.

Prodrugs comprising acid labile components for release of the therapeutic or toxic component are frequently used in pharmaceutical research and application. In the field of antibody drug conjugates (ADCs) acid labile linkers enable the release of the toxic payload after targeting the construct to a tumor cell by the target-specific antibody. The concept involves a receptor mediated endocytosis (cellular uptake) of the ADC followed by an intracellular trafficking to the lysosomes. Once an ADC binds to its surface tumor antigen, it is internalized into endosomes that subsequently mature and fuse with lysosomes; in the lysosomes, the drug is released via cleavage of the linker by specific proteases such as cathepsin B or by the degradation of the ADC. Lysosomes are characterized by an acidic pH of 4-5 (Chalouni and Doll, 2018), thought to be acidic enough for hydrolysis of the acid labile bond. Acid labile linkers like acyl-hydrazones were successfully used in ADCs which received market authorization (Chalouni and Doll, 2018).

Other acid labile groups like acetals have been considered as components of linkers for ADCs. While molecules comprising acyclic acetals based on aliphatic aldehydes or ketones have shown to be cleavable at pH 5, cyclic acetales of aliphatic carbonyl compounds have not been studied yet in this respect; these structures might have a to high stability, and release by acidic intracellular environment seems doubtful.

WO2014/135282 discloses methods for the preparation of amatoxins comprising cyclic carbonates and cyclic acetals with improved properties for use as ADCs but does not teach compounds with controllable release mechanisms.

Gillies et al. (2004) describe five- or six-membered cyclic acetals based on benzaldehyde derivatives included in low molecular weight prodrugs. Other than aliphatic acetals, introduction of an aromatic substituent to the acetalic carbon atom enables the modulation of the acidic stability by further substituents. The Hammett's rule allows for a prediction of the reactivity of benzylic acetals in relation to the substitution pattern of the aromatic ring. By following this principle, a cyclic acetal with half-live ranging from 17.6 h at pH 5.0 and several weeks at pH 7.4 could be synthesized.

WO2015/152182 (NOF Corporation) describes hydrophilic polymer derivatives having cyclic benzylidene acetal linkers whose hydrolysis rate at pH of a weakly acidic environment in the living body can be controlled via position and nature of substituents at the benzylic structure; in particular possible acid labile linkers for polymer drug conjugates based on five- or six-membered cyclic acetales from benzaldehyde derivatives are disclosed. The document does not disclose any specific example of cytotoxic payload and biological data. Furthermore, the teaching of WO2015/152182 requires additional moieties for covalent linkage of the cyclic acetal to the drug compound. These linker structures are not involved in the acidic cleavage and remain connected to the released payload, presumably with negative impact on the pharmacodynamic activity of the same.

Since cleavage of cyclic acetals disclosed in the prior art requires an acidic environment, it is essential that the construct is taken up by the cell and transported to lysosomes, where only appropriate acidic conditions are found. Therefore, the cyclic acetals disclosed in the prior art are limited to target binding moieties that result in efficient uptake after receptor binding.

However, other promising target structures remain on the cell surface upon binding of the target binding moiety and/or are not transported to late endosomes and lysosomes after uptake, and thus might not be amenable to this technology.

A combination of a cleavable peptide structure and a self-immolative spacer between the targeting-binding antibody and the drug of an ADC has been described to be applicable to a payload carrying a primary or secondary amine. Jeffrey et al. (2005) and WO2016/142049 disclose para-aminobenzyl ether linkers that are applicable for phenolic moieties. Carboxylic acids of the payload can be addressed by analogous para-aminobenzyl amides (WO 2017/149077).

Another type of related self immolative moieties frequently used for small molecular prodrugs has been disclosed in Tranoy-Opalinski et al. (2014), wherein the specific side chain comprises a β-glucuronide and after enzymatic cleavage by β-glucuronidase, starting at the then terminal phenolic moiety, is undergoing a spontaneous fragmentation. Linkers of this type are also used in the ADC field and are, e.g., described in Jeffrey et al. (2006).

SUMMARY OF THE INVENTION

In view of the prior art, it is hence one object of the present invention to provide a highly efficient release mechanism of a drug from a prodrug under controlled conditions that allows for rest-free release of the drug, thus increasing therapeutic efficiency and avoiding loss of drug activity due to chemical residues remaining on the released therapeutic agent.

It is one object of the present invention to provide a target-binding moiety amatoxin conjugate comprising an efficient, pH-independent release mechanism for rest-free release of highly active amatoxin.

It is another object of the present invention to provide modified amatoxins for synthesis of said conjugates.

It is still another object of the present invention to provide improved target-binding moiety amatoxin conjugates for therapeutic use, in particular for tumor therapy and oncology.

These objects are achieved with methods and means according to the independent claims of the present invention. The dependent claims are related to preferred embodiments.

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure and avoid lengthy repetitions.

The present invention provides solutions to the limitations as described above with regard to controllable, rest-free release of drugs from prodrugs, in particular from antibody-drug conjugates (ADCs).

Figure 1:
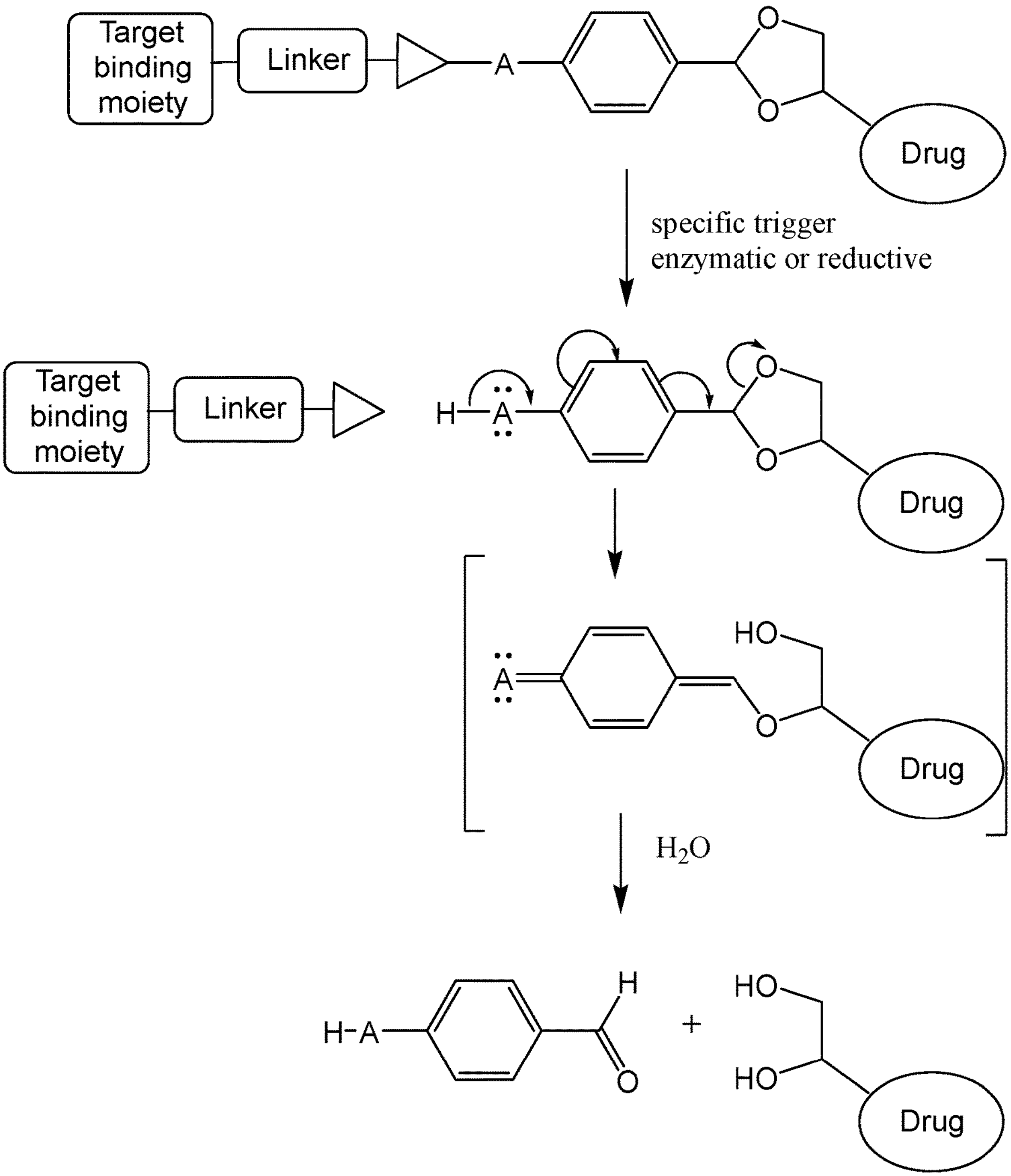
FIG. 1. Schematic representation of the drug release mechanism in linker systems of the present invention. The triangle represents an enzymatically cleavable structure, preferably a peptidic structure. A is an electron donating group that can be selected from, but is not limited to, O, NH or S.

The present invention relates to a specific drug release mechanism for improvement of prodrug systems applied in targeted therapies like antibody-drug conjugates or peptide drug conjugates. Prodrugs according to the current invention are comprising benzylic five- or six-membered cyclic acetals combined with an electron donating group and a side chain comprising and/or representing a specific cleavage side. Cleavage of said cleavage site triggers an assisted release of the acetals, resulting in the liberation of rest-free drug (FIG. 1).

Various cytotoxic drugs like amatoxins, aphidicolin, apoptolidin, calicheamicins, digitoxin, digoxin, etoposide, glucopiericidin A, hypothemycin, isatropolone A, lactacystin, muscotoxin A, pancratistatin, phalloidins, phenpanstatin, phytosphingosine, poscillaridin A, pseurotin A, rebeccamycin, sinefungin, G-strophanthin, swainsonine, turbostatin 1-4, and others, are comprising 1,2- and 1,3-diol structures which can be used for formation of cyclic acetals. This at least one 1,2- or 1,3-diol moiety is being restored when the drug is released from the compounds according to the present invention.

The current invention relates to compounds comprising and methods for introduction of benzylic cyclic acetals with enhanced hydrolysis after cleavage of a specific side chain, resulting in a moiety in 1-2- (ortho-) or 1-4 (para-) positions of the acetalic carbon with a strong positive mesomeric effect. Enzymatic cleavage of the side chain comprising and/or representing a specific cleavage side (e.g., peptide) releases the electron donating group (e.g., 2- or 4-amino group) with strong electron donating properties, resulting in spontaneous fragmentation of the benzylidene linker and the diol via ortho or para quinone intermediates to liberate the free payload.

Enzymatic cleavage is performed by specific proteases, e.g., cathepsins, preferably cathepsin B, elastase or matrix metalloproteases. In some embodiments, said proteases are tumor specific enzymes in the extracellular matrix, like matrix metalloproteases or β-glucuronidase.

Surprisingly the inventors found that a combination of cleavable linker elements and self-immolative moieties could successfully be applied to cyclic acetals in prodrugs, in particular in amatoxin comprising ADCs. The compounds and methods of the present invention allow for the efficient, controllable, pH-independent release of drugs from prodrugs, in particular from amatoxin comprising ADCs, at cyclic acetals in a manner that the released drug moiety is free of remaining residues or structural elements from spacer, linker or target-binding moieties which might impose the risk of reducing drug activity and therapeutic efficiency.

According to one aspect, the invention relates to a compound of Formula I or II comprising a cytotoxic drug moiety

I

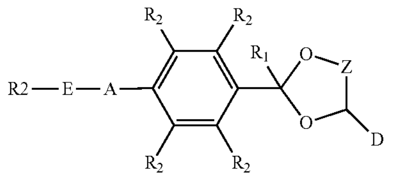

-continued

II

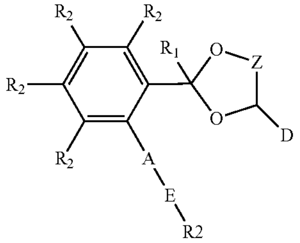

wherein

D is a cytotoxic drug moiety comprising at least one 1,2- or 1,3-diol moiety upon release from the compound;

Z is $CH_2$, $CH_2$—$CH_2$ or CHR3-CHR3, wherein R3 is independently H or an alkyl group, optionally substituted by heteroatoms;

R1 is H or a $C_1$-$C_6$ alkyl group;

A is an electron donating group;

E is a cleavage site;

R2 are independently H or electron withdrawing or donating groups.

The cytotoxic drug according to the present invention can be selected from, e.g., but is not limited to, amatoxin, aphidicolin, apoptolidin, calicheamicins, digitoxin, digoxin, etoposide, glucopiericidin A, hypothemycin, isatropolone A, lactacystin, muscotoxin A, pancratistatin, phalloidins, phenpanstatin, phytosphingosine, poscillaridin A, pseurotin A, rebeccamycin, sinefungin, G-strophanthin, swainsonine, and turbostatin 1-4.

Amatoxins are cyclic peptides composed of 8 amino acids. They can, for example, be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA polymerase II is very tight (KD=3 nM). Dissociation of amanitin from the enzyme is a very slow process, thus making recovery of an affected cell unlikely. When the inhibition of transcription lasts too long, the cell will undergo programmed cell death (apoptosis).

As used herein, the term "amatoxin" shall include all cyclic peptides composed of 8 amino acids as isolated from the genus *Amanita* and described in Wieland, T. and Faulstich H. (Wieland T, Faulstich H., CRC Crit Rev Biochem. 1978 December; 5(3): 185-260), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in which the thioether sulfoxide moiety is replaced by a sulfide, sulfone, or by atoms different from sulfur, e.g. a carbon atom as in a carba-analogue of amanitin, in each case wherein any such derivative or analogue is functionally active by inhibiting mammalian RNA polymerase II.

As used herein, a "derivative" of a compound refers to a species having a chemical structure that is similar to the compound, yet containing at least one chemical group not present in the compound and/or deficient of at least one chemical group that is present in the compound. The compound to which the derivative is compared is known as the "parent" compound. Typically, a "derivative" may be produced from the parent compound in one or more chemical reaction steps.

As used herein, an "analogue" of a compound is structurally related but not identical to the compound and exhibits at least one activity of the compound. The compound to which the analogue is compared is known as the "parent" compound. The afore-mentioned activities include, without limitation: binding activity to another compound; inhibitory activity, e.g. enzyme inhibitory activity; toxic effects; activating activity, e.g. enzyme-activating activity. It is not required that the analogue exhibits such an activity to the same extent as the parent compound. A compound is regarded as an analogue within the context of the present application, if it exhibits the relevant activity to a degree of at least 1% (more preferably at least 5%, more preferably at least 10%, more preferably at least 20%, more preferably at least 30%, more preferably at least 40%, and more preferably at least 50%) of the activity of the parent compound. Thus, an "analogue of an amatoxin", as it is used herein, refers to a compound that is structurally related to any one of α-amanitin, β-amanitin, γ-amanitin, ε-amanitin, amanin, amaninamide, amanullin, and amanullinic acid and that exhibits at least 1% (more preferably at least 5%, more preferably at least 10%, more preferably at least 20%, more preferably at least 30%, more preferably at least 40%, and more preferably at least 50%) of the inhibitory activity against mammalian RNA polymerase II as compared to at least one of α-amanitin, β-amanitin, γ-amanitin, ε-amanitin, amanin, amaninamide, amanullin, and amanullinic acid. An "analogue of an amatoxin" suitable for use in the present invention may even exhibit a greater inhibitory activity against mammalian RNA polymerase II than any one of α-amanitin, β-amanitin, γ-amanitin, ε-amanitin, amanin, amaninamide, amanullin, or amanullinic acid. The inhibitory activity might be measured by determining the concentration at which 50% inhibition occurs ($IC_{50}$ value). The inhibitory activity against mammalian RNA polymerase II can be determined indirectly by measuring the inhibitory activity on cell proliferation.

A "semisynthetic analogue" refers to an analogue that has been obtained by chemical synthesis using compounds from natural sources (e.g. plant materials, bacterial cultures, fungal cultures or cell cultures) as starting material. Typically, a "semisynthetic analogue" of the present invention has been synthesized starting from a compound isolated from a mushroom of the Amanitaceae family. In contrast, a "synthetic analogue" refers to an analogue synthesized by so-called total synthesis from small (typically petrochemical) building blocks. Usually, this total synthesis is carried out without the aid of biological processes.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined above. Amatoxins which are particularly suitable for the conjugates of the present invention are α-amanitin, β-amanitin, γ-amanitin, ε-amanitin, amanin, amaninamide, amanullin, and amanullinic acid as well as salts, chemical derivatives, semisynthetic analogues, and synthetic analogues thereof. Particularly preferred amatoxins for use in the present invention are α-amanitin, β-amanitin, and amaninamide.

According to one aspect of the invention, the amatoxin can be selected from the group consisting of α-amanitin, β-amanitin, amanin, amaninamide and analogues, derivatives and salts thereof.

As used herein, the term "electron donating group" shall refer to nitrogen, oxygen, sulfur or substituents having lone pairs of electrons that can be donated to the aromatic π-electrons system like amines (NH2, NHR, NR2), phenol (OH) and its conjugate base O-, Alkoxy-groups (OR), phenylesters (OCOR) or thiols, as well as alkylgroups with a positive inductive effect.

The term "electron withdrawing group" shall refer to substituents that exhibit a negative mesomeric effect on the aromatic π-system like halogens, nitro-, carbonyl-, cyano- and sulfonyl groups or groups with a negative inductive effect like trifluoromethyl or trialkylammonium groups.

According to one aspect of the invention, the electron donating group A is selected from O, NH and S.

As used herein, the term "cleavage site" shall refer to a moiety that is susceptible to specific cleavage at a defined position under particular conditions. Said conditions are, e.g., specific enzymes or a reductive environment in specific body or cell compartments.

According to one aspect of the invention, the cleavage site E is an enzymatically cleavable moiety comprising two or more amino acids. Preferably, said enzymatically cleavable moiety comprises a valine-alanine (Val-Ala), valine-citrulline (Val-Cit), valine-lysine (Val-Lys), valine-arginine (Val-Arg) dipeptide, a phenylalanine-lysine-glycine-proline-leucin-glycine (Phe Lys Gly Pro Leu Gly) or alanine-alanine-proline-valine (Ala Ala Pro Val) peptide, or a β-glucuronide or β-galactoside.

According to one embodiment, said cleavage site is cleavable by at least one agent selected from the group consisting of cysteine protease, metalloprotease, serine protease, threonine protease, and aspartic protease.

Cysteine proteases, also known as thiol proteases, are proteases that share a common catalytic mechanism that involves a nucleophilic cysteine thiol in a catalytic triad or dyad.

Metalloproteases are proteases whose catalytic mechanism involves a metal. Most metalloproteases require zinc, but some use cobalt. The metal ion is coordinated to the protein via three ligands. The ligands co-ordinating the metal ion can vary with histidine, glutamate, aspartate, lysine, and arginine. The fourth coordination position is taken up by a labile water molecule.

Serine proteases are enzymes that cleave peptide bonds in proteins; serine serves as the nucleophilic amino acid at the enzyme's active site. Serine proteases fall into two broad categories based on their structure: chymotrypsin-like (trypsin-like) or subtilisin-like.

Threonine proteases are a family of proteolytic enzymes harbouring a threonine (Thr) residue within the active site. The prototype members of this class of enzymes are the catalytic subunits of the proteasome, however, the acyltransferases convergently evolved the same active site geometry and mechanism.

Aspartic proteases are a catalytic type of protease enzymes that use an activated water molecule bound to one or more aspartate residues for catalysis of their peptide substrates. In general, they have two highly conserved aspartates in the active site and are optimally active at acidic pH. Nearly all known aspartyl proteases are inhibited by pepstatin.

In particular embodiments the cleavable site is cleavable by at least one agent selected from the group consisting of Cathepsin A or B, matrix metalloproteinases (MMPs), elastase, β-glucuronidase and β-galactosidase.

In another aspect of the invention, the cleavage site E is a disulfide bond and specific cleavage is conducted by a reductive environment, e.g. an intracellular reductive environment.

In another aspect, the present invention relates to a conjugate comprising the compound according to the present invention and a T-L moiety, wherein said T-L moiety is substituting at least one of residues R2 in Formula I or II, and wherein L is a linker and T is a target binding moiety.

As used herein, the term "linker" shall refer to a bifunctional group that can covalently connect the target binding moiety to the compound according to the present invention comprising a cytotoxic drug moiety.

The linker L according to the present invention may comprise or may consist of an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted. The linker can also be only a covalent bondage.

In one aspect according to the present invention, the linker L comprises a moiety selected from at least one of the following moieties: a disulfide, an ether, a thioether, an amine, an ester, a carboxamide, a urethane, and a urea moiety.

A "linker" in the context of the present application refers to a molecule that increases the distance between two components, e.g. to alleviate steric interference between the target binding moiety and the compound according to the present invention, e.g., an amatoxin or amatoxin derivative, which may otherwise decrease the ability of the amatoxin to interact with RNA polymerase II. The linker may serve another purpose as it may facilitate the release of the amatoxin specifically in the cell being targeted by the target binding moiety. It is preferred that the linker and preferably the bond between the linker and the compound according to the present invention, preferably an amatoxin on one side and the bond between the linker and the antibody on the other side is stable under the physiological conditions outside the cell, e.g. the blood, while it can be cleaved inside the cell, in particular inside the target cell, e.g. cancer cell or immune cell. To provide this selective stability the linker may comprise functionalities that are preferably pH sensitive or protease sensitive. Alternatively, the bond linking the linker to the target binding moiety may provide the selective stability. Preferably a linker has a length of at least 1, preferably of 1-30 atoms length (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 atoms) wherein one side of the linker has been reacted with the amatoxin and, the other side with a target-binding moiety. In the context of the present invention, a linker preferably is a C1-30-alkyl, C1-30-heteroalkyl, C2-30-alkenyl, C2-30-heteroalkenyl, C2-30-alkynyl, C2-30-heteroalkynyl, cycloalkyl, heterocycloalkyl, aryl, heteroaryl, aralkyl, or a heteroaralkyl group, optionally substituted. The linker may contain one or more structural elements such as amide, ester, ether, thioether, disulfide, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the target binding moiety. To that end the linker to be will carry two groups, preferably at a proximal and distal end, which can (i) form a covalent bond to a group, preferably an activated group on an amatoxin or the target binding-peptide or (ii) which is or can be activated to form a covalent bond with a group on an amatoxin. Accordingly, if the linker is present, it is preferred that chemical groups are at the distal and proximal end of the linker, which are the result of such a coupling reaction, e.g. an ester, an ether, a urethane, a peptide bond etc.

As used herein, the term "target binding moiety" shall refer to any molecule or part of a molecule that can specifically bind to a target molecule or target epitope. Target-binding moieties suitable for use in the present invention typically have a molecular mass of 40 000 Da (40 kDa) or more.

As used herein, the terms "target molecule" and "target epitope", respectively, refers to an antigen and an epitope of an antigen, respectively, that is specifically bound by a target-binding moiety. Preferably the target molecule is a tumor-associated antigen, in particular an antigen or an epitope which is present on the surface of one or more tumor cell types or tumor-associated cells in an increased concentration and/or in a different steric configuration as compared to the surface of non-tumor cells. Preferably, said antigen or epitope is present on the surface of one or more tumor or tumor stroma cell types, but not on the surface of non-tumor cells. In other embodiments, said antigen or epitope is preferentially expressed on cells involved in autoimmune diseases. In other embodiments, said antigen or epitope is preferentially expressed on cells involved in an inflammatory disease.

In one aspect according to the present invention, the target binding moiety T is selected from the group consisting of (i) an antibody or antigen-binding fragment thereof, (ii) an antibody-like protein, and (iii) a nucleic acid aptamer.

The term "antibody or antigen binding fragment thereof", as used herein, refers to immunoglobulin molecules and immunologically active portions of immunoglobulin molecules, i.e., molecules that contain an antigen binding site that specifically binds an antigen. Also comprised are immunoglobulin (Ig)-like proteins that are selected through techniques including, for example, phage display to specifically bind to a target molecule, e.g. to the target protein Her-2/neu or EpCAM. The immunoglobulin molecules of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Antibodies and antigen-binding fragments thereof suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, $F(ab')_2$ fragments, fragments produced by a Fab expression library, diabodies or tetrabodies (Poljak R. J., 1994), nanobodies, anti-idiotypic (anti-Id) antibodies (including, e.g., anti-Id antibodies to antibodies of the invention), and epitope-binding fragments of any of the above.

In one aspect according to the present invention, the antibody or the antigen-binding fragment thereof is selected from a diabody, a tetrabody, a nanobody, a chimeric antibody, a deimmunized antibody, a humanized antibody or a human antibody.

In one aspect according to the present invention, the antigen binding fragment is selected from the group consisting of Fab, F(ab')2, Fd, Fv, single-chain Fv, disulfide-linked Fvs (dsFv) and fragments comprising at least one VL and/or VH domain.

As used herein, the term "antibody-like protein" refers to a protein that has been engineered (e.g. by mutagenesis of Ig loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (Binz et al., 2005). Antibody-like proteins can be derived from large libraries of mutants, e.g. by panning from large phage display libraries, and can be isolated in analogy to regular antibodies. Also, antibody-like binding proteins can be obtained by combinatorial mutagenesis of surface-exposed residues in globular proteins.

As used herein, the term "nucleic acid aptamer" refers to a nucleic acid molecule that has been engineered through repeated rounds of in vitro selection or SELEX (systematic evolution of ligands by exponential enrichment) to bind to a target molecule (Wang et al., 2019). The nucleic acid aptamer may be a DNA or an RNA molecule. The aptamers may contain modifications, e.g. modified nucleotides such as 2'-fluorine-substituted pyrimidines.

In one aspect, the present invention relates to a conjugate of Formula III or IV

III

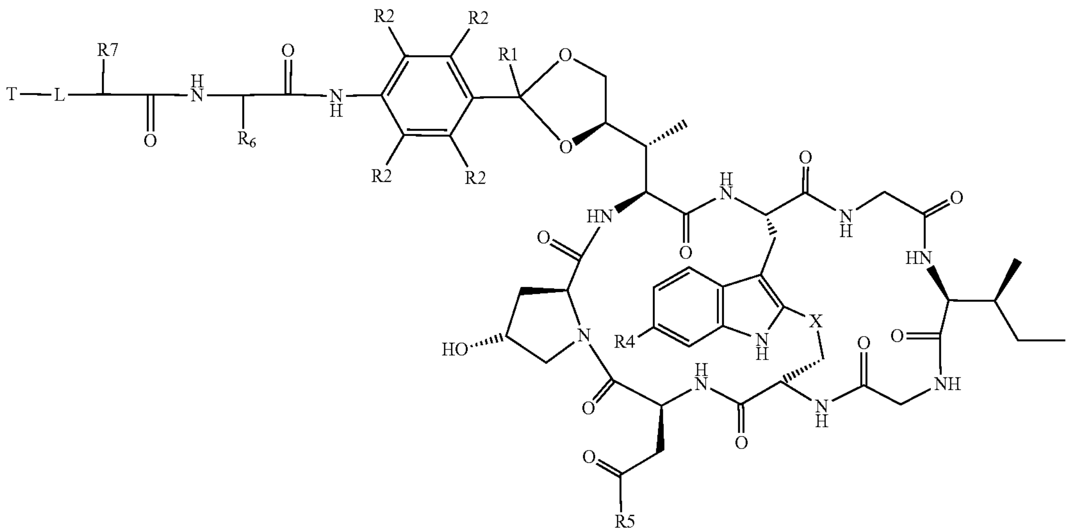

-continued

IV

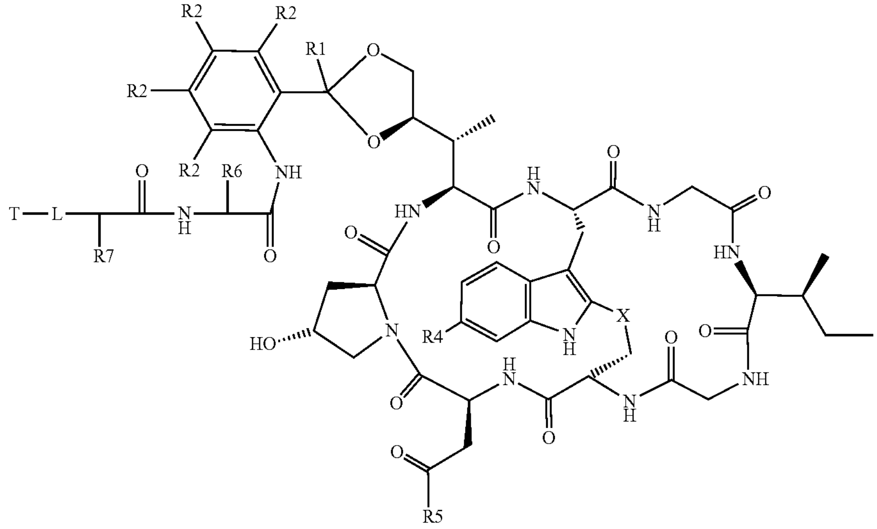

wherein

X is S, SO or $SO_2$;

R1 is H or a $C_1$-$C_6$ alkyl group;

R2 are independently H or electron withdrawing or donating groups;

R4 is H, OH, O—$C_1$-$C_8$-alkyl, $NO_2$, $NH_2$, F, Cl, Br, or SH;

R5 is OH, $NH_2$, or NHOH;

R6, R7 are side chains of natural or unnatural amino acids;

L is a linker, and

T is a target binding moiety.

Conjugates of Formula III or IV release their payload (cytotoxic drug) after peptide cleavage at the anilide site by peptidases such as, but not limited to, cathepsines, elastase or matrix metalloproteases.

In another aspect, the present invention relates to a conjugate of Formula V

V

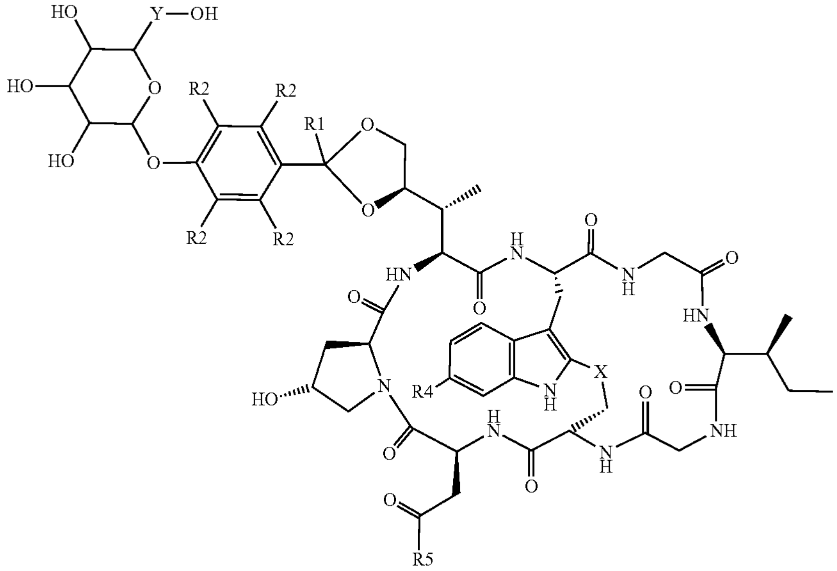

wherein

X is S, SO or $SO_2$;

Y is $CH_2$ or CO;

R1 is H or a $C_1$-$C_6$ alkyl group;

R2 are independently H or electron withdrawing or donating groups; wherein at least one R2 group is substituted by said T-L moiety R4 is H, OH, O—$C_1$-$C_8$-alkyl, $NO_2$, $NH_2$, F, Cl, Br, or SH;

R5 is OH, $NH_2$, or NHOH;

L is a linker, and

T is a target binding moiety.

Conjugates of Formula V release their payload (cytotoxic drug) after glycoside cleavage by enzymes such as, but not limited to, β-glucuronidase or β-galactosidase.

In another aspect, the present invention relates to a conjugate of Formula VI

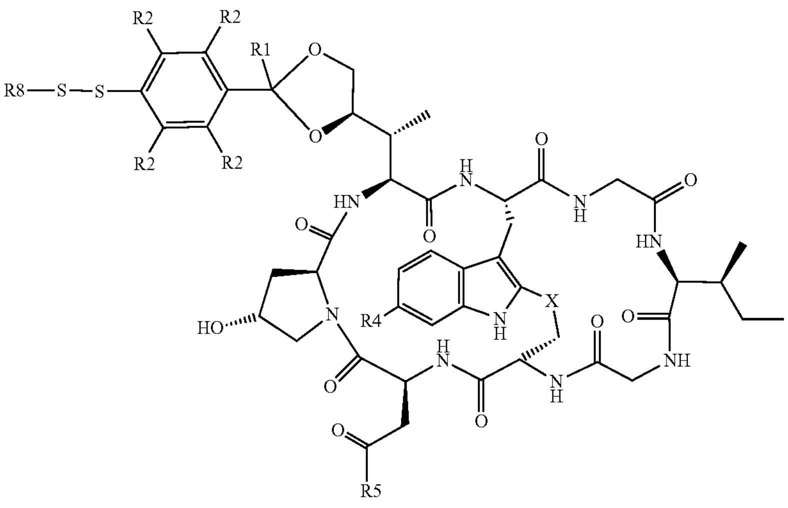

VI wherein

X is S, SO or $SO_2$;

R1 is H or a $C_1$-$C_6$ alkyl group;

R2 are independently H or electron withdrawing or donating groups, except one R2 is substituted by said T-L-moiety, if R8 is not a T-L-moiety;

R4 is H, OH, O—$C_1$-$C_8$-alkyl, $NO_2$, $NH_2$, F, Cl, Br, or SH;

R5 is OH, $NH_2$, or NHOH;

R8 is a linear or branched alkyl group, or, if no R2 is a T-L-moiety, is a T-L-moiety;

L is a linker and

T is a target binding moiety.

Conjugates of Formula VI release their payload (cytotoxic drug) after disulfide cleavage by a reductive environment, e.g., a reductive intracellular environment.

In another aspect, the present invention relates to a conjugate of Formula VII

VII

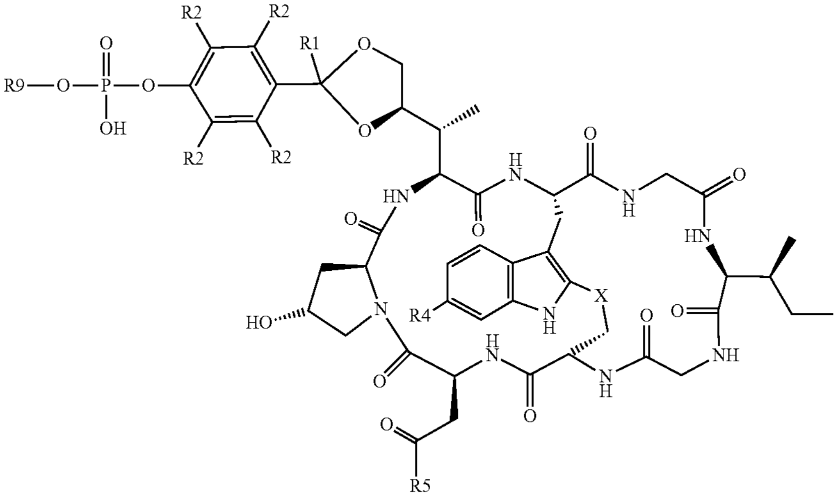

wherein

X is S, SO or $SO_2$;

R1 is H or a $C_1$-$C_6$ alkyl group;

R2 are independently H or electron withdrawing or donating groups, except one R2 is substituted by said T-L-moiety, if R9 is not a T-L-moiety;

R4 is H, OH, O—$C_1$-$C_8$-alkyl, $NO_2$, $NH_2$, F, Cl, Br, or SH;

R5 is OH, $NH_2$, or NHOH;

R9 is H or a linear or branched alkyl group or, if no R2 is a T-L-moiety, is a T-L-moiety;

L is a linker and

T is a target binding moiety.

Conjugates of Formula VII release their payload (cytotoxic drug) after enzymatic cleavage of the phosphate ester.

In another aspect, the present invention relates to a conjugate of Formula VIII

VIII

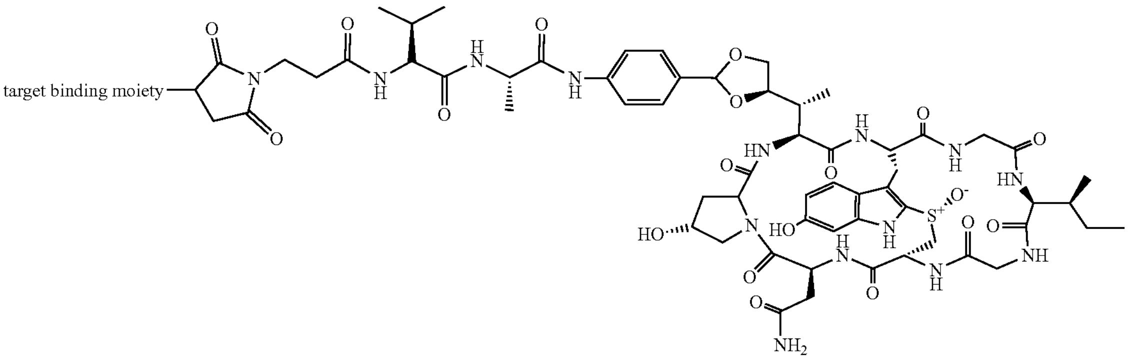

In a further aspect, the present invention relates to compounds of Formula IX or X

IX

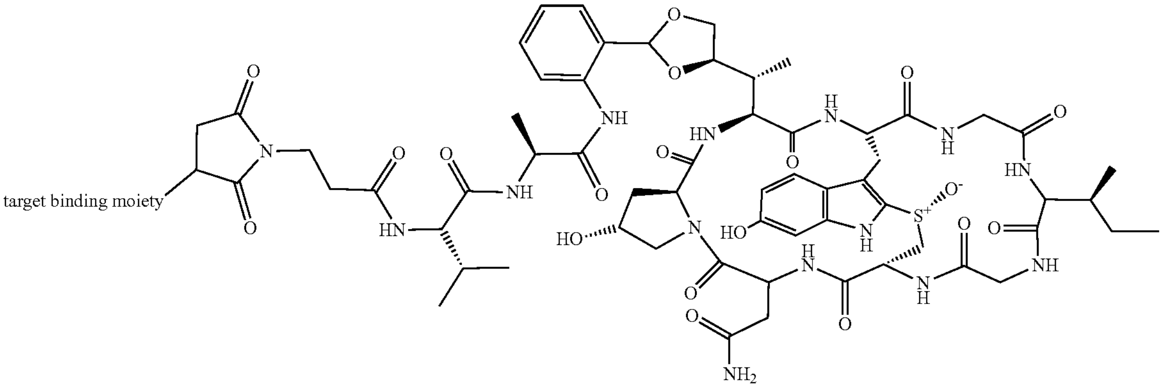

X

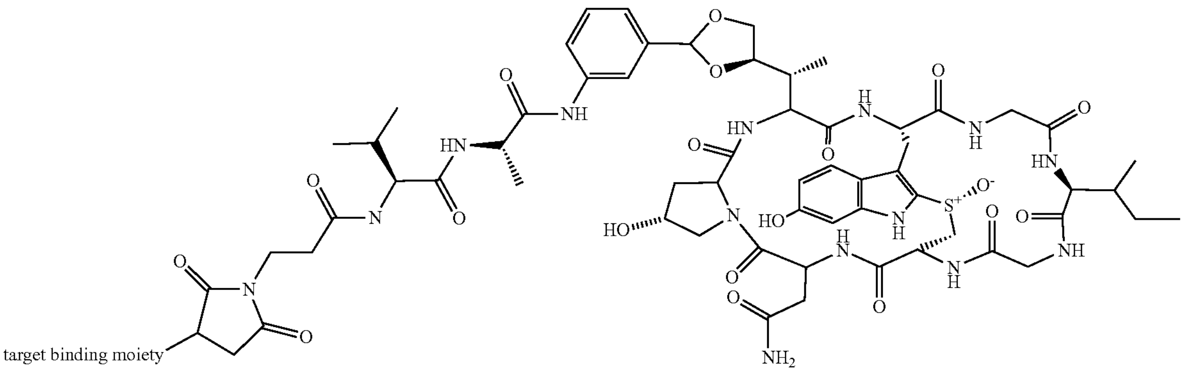

In another aspect the present invention relates to a conjugate of the present invention for use as a medicament.

In another aspect the present invention relates to a method for synthesizing the conjugates according to the present invention by reacting a 1,2- or 1,3-diol with a dimethyl benzylidene acetal in an aprotic solvent under acidic conditions.

The invention preferably relates to a method for synthesizing the conjugates according to the present invention by reacting an amatoxin with a dimethyl benzylidene acetal in an aprotic solvent under acidic conditions. Said amatoxin is selected preferably from the group consisting of alpha-amanitin, beta-amanitin, amanine, amaninamide and their respective thioethers.

In a preferred embodiment, said method according to the present invention relates to a method wherein the aprotic solvent is DMF and/or the acid is trifluoroacetic acid.

As used herein, the term "under acidic conditions" shall refer to a pH of 5.0 or below. Particularly preferred, the method is performed at a pH of about 5.0, 4.5, 4.0, 3.5, 3.0, 2.5, 2.0, 1.5, or 1.0.

Cyclic acetals can be formed by reaction of an aldehyde or ketone with a diol compound under acidic conditions. Typically, these reactions need elevated temperatures and removal of water formed as byproduct by means of azeotropic distillation or water binding agents like calcium sulfate or molecular sieves. Such methods are often impractical when using sensitive and valuable starting materials. In such cases, it is advantageous to pre-activate the less sensitive and less expensive component as an acylic acetal. Formation of the cyclic acetal can then be achieved by a catalytic amount of acid preferred by the entropy effect in the formation of a cyclic from an acyclic compound.

For the cyclic acetals of the current invention the diol is usually the more valuable and less stable compound. Therefore, the aromatic carbonyl group is preferably converted to the acyclic acetal with a low boiling alcohol like methanol, ethanol, propanol, butanol or trifluoroethanol in presence of a water binding agent. More preferably, the water binding agent is an orthoester and the solvent is a low boiling alcohol. Preferred orthoesters are trimethyl orthoformate, triethyl orthoacetate, triethyl orthoformate, triethyl orthoacetate or tripropyl orthoformate. Most preferred is the use of trimethyl orthoformate.

Acidic catalysts are preferably water free acids like concentrated sulfuric acid, hydrogen chloride in an organic solvent, e.g., HCl/EtOH, HCl/MeOH, HCl/1,4-dioxane etc., 4-toluenesulfonic acid, trifluoracetic acid or polymeric sulfonic acids like strong cation exchangers in the protonated form, e.g Dowex® 50 W X8, Amberlite® IR-120 and alike. Most preferred is the use of hydrogen chloride in 1,4-dioxan and 4-toluenesulfonic acid.

Reaction of the acyclic acetal with the diol compound is preferably performed in a high-boiling aprotic solvent like DMSO, DMF, DMA, NMP, 1,4-dioxan xylene or toluene. Preferred is the use of DMF. The acidic catalyst in this reaction can be chosen from the list above. Preferred are acids with low boiling point like HCl/1,4-dioxan or trifluoracetic acid. Most preferred is the use of trifluoracetic acid.

In another aspect the present invention relates to a conjugate of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

In still another aspect the present invention relates to a pharmaceutical composition comprising the conjugate according to the present invention, optionally further comprising one or more pharmaceutically acceptable diluents, carriers, excipients, fillers, binders, lubricants, disintegrants, adsorbents; and/or preservatives.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c), intramuscular (i.m.), intravenous (i.v.) or intracutaneous (i.e.) application. In particular, it is possible to produce the respectively suitable injection formulations as a suspension of crystals, solutions, nanoparticular or a colloid dispersed systems like, e.g. hydrosols.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Example 1: 4-Dimethoxymethyl-phenol (HDP 30.2628)

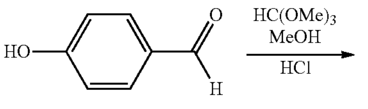

4-Hydroxy benzaldehyde

-continued

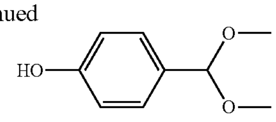

HDP 30.2628

4-Hydroxy benzaldehyde (1.221 g, 10 mmol) was dissolved in 30 ml methanol, 10.9 ml (100 mmol) trimethyl orthoformate and 250 μl (1 mmol) Hydrogen chloride solution 4M in Dioxan were added and the solution was heated under reflux for 1 h. TLC control (n-hexane/ethyl acetate 1:1) indicated complete conversion of aldehyde (Rf=0.36) to dimethylacetal (Rf=0.45). After rotary evaporation to 10 ml the reaction was quenched with 50 ml saturated sodium bicarbonate solution and the mixture was extracted with 50 ml ethyl acetate. The organic layer was washed with 50 ml brine, dried over $MgSO_4$ and evaporated to a 1.739 mg 4-Dimethoxymethyl-phenol as an oil. The product was homogenous by TLC and HPLC and was used for the next step without further purification.

Example 2: 3-Dimethoxymethyl-phenol (HDP 30.2629)

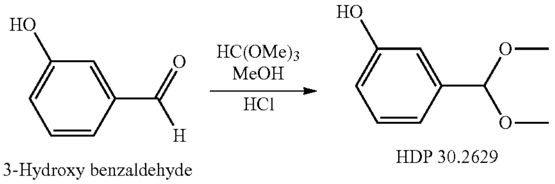

3-Hydroxy benzaldehyde

HDP 30.2629

By applying the procedure of example 1 on 3-hydroxy benzaldehyde, the 3-dimethoxymethyl-phenol was obtained in quantitative yield.

Example 3: 4-Dimethoxymethyl-2-fluoro-phenol (HDP 30.2630)

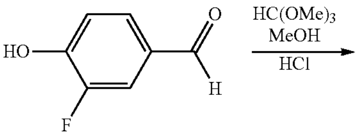

3-Fluoro-4-hydroxybenzaldehyde

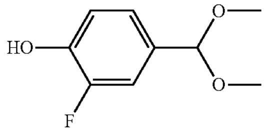

HDP 30.2630

By applying the procedure of example 1 on 1 g (7.14 mmol) 3-fluoro-4-hydroxy benzaldehyde, the 4-Dimethoxymethyl-2-fluoro-phenol was obtained in quantitative yield.

Example 4: 4-Bromo-3-dimethoxymethyl-phenol (HDP 30.2631)

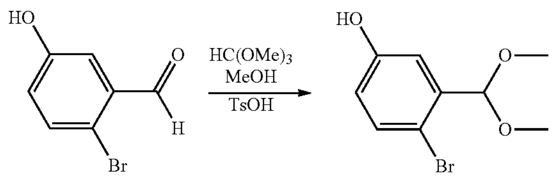

2-Bromo-3-hydroxybenzaldehyde

HDP 30.2631

By applying the procedure of example 1 on 2-Bromo-3-hydroxybenzaldehyde, the 4-Bromo-3-dimethoxymethyl-phenol was obtained in quantitative yield.

Example 5: 1-[11-bromo-3,6,9-trioxaundecyloxy]-4-dimethoxymethyl-benzene (HDP 30.2637)

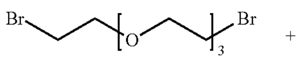

HDP 30.0381

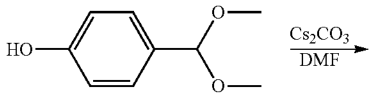

HDP 30.2628

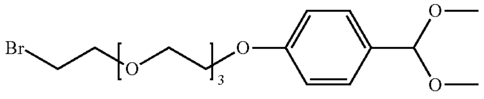

HDP 30.2637

The crude 4-Dimethoxymethyl-phenol from Example 1: (1,739 g, max. 10 mmol) and 6.400 g (20 mmol) 1,11-Dibromo-3,6,6-trioxaundecane were dissolved in 40 ml dry DMF and 3.910 g (12 mmol) cesium carbonate was added and the mixture was heated to 50° C. for 1 h. The DMF was evaporated subsequently and the remaining was stirred in 50 ml dichloromethane, followed by filtration. The filtrate was evaporated and purified on silica gel with a gradient of n-hexane to ethyl acetate, to receive 1.862 g (46%) product 1-[11-bromo-3,6,9-trioxaundecyloxy]-4-dimethoxymethyl-benzene as an oil.

$^1$H NMR (500 MHz, $CDCl_3$) d 7.39-7.32 (m, 2H), 6.94-6.87 (m, 2H), 5.35 (s, 1H), 4.17-4.11 (m, 2H), 3.91-3.84 (m, 2H), 3.80 (t, J=6.3 Hz, 2H), 3.76-3.71 (m, 2H), 3.71-3.66 (m, 6H), 3.46 (t, J=6.3 Hz, 2H), 3.31 (s, 6H).

$^{13}$C NMR (126 MHz, $CDCl_3$) d 158.85, 130.53, 127.88, 114.21, 102.99, 71.19, 70.84, 70.70, 70.64, 70.53, 69.73, 67.42, 52.59, 30.33.

MS (ESI$^+$) found.: 429.17; calc. for $[M+Na]^+$: 429.09 ($C_{17}H_{27}BrNaO_6$).

Example 6: 1-[11-bromo-3,6,9-trioxaundecyloxy]-3-dimethoxymethyl-benzene (HDP 30.2641)

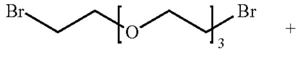

HDP 30.0381

-continued

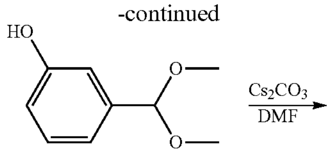

HDP 30.2629

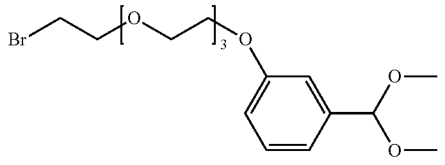

HDP 30.2641

By applying the procedure of example 5 on the crude product of example 2, 2.079 g (51%) title compound (HDP 30.2641) was achieved as an oil.

$^1$H NMR (500 MHz, $CDCl_3$) d 7.30-7.23 (m, 1H), 7.06-7.00 (m, 2H), 6.88 (ddd, J=8.3, 2.5, 1.1 Hz, 1H), 5.35 (s, 1H), 4.17-4.12 (m, 2H), 3.88-3.84 (m, 2H), 3.81 (t, J=6.3 Hz, 2H), 3.77-3.71 (m, 2H), 3.71-3.66 (m, 6H), 3.46 (t, J=6.3 Hz, 2H), 3.32 (s, 6H).

$^{13}$C NMR (126 MHz, $CDCl_3$) d 158.92, 139.76, 129.32, 119.38, 115.01, 112.74, 103.06, 71.31, 70.95, 70.82, 70.76, 70.65, 69.87, 67.54, 52.84, 30.44.

MS (ESI$^+$) found.: 375.17/377.17; calc. for $[MH-OMe]^+$: 375.08/377.08 ($C_{16}H_{24}BrO_5$).

Example 7: 1-(11-bromo-3,6,6-trioxaundecyl)-4-dimethoxymethyl-2-fluoro-benzene (HDP 30.2642)

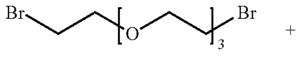

HDP 30.0381

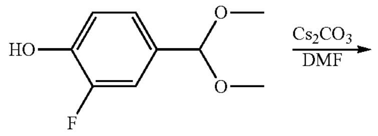

HDP 30.2630

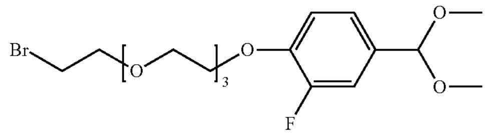

HDP 30.2642

By applying the procedure of example 5 on the crude product of example 3, 2.032 g (67%) title compound (HDP 30.2642) was achieved as an oil.

MS (ESI$^+$) found.: 393.17/395.17; calc. for $[MH-OMe]^+$: 393.07/395.07 ($C_{16}H_{23}BrFO_5$).

$^1$H NMR (500 MHz, $CDCl_3$) d 7.18 (dd, J=12.0, 2.1 Hz, 1H), 7.13 (ddt, J=8.4, 1.9, 0.8 Hz, 1H), 6.97 (t, J=8.4 Hz, 1H), 5.33 (s, 1H), 4.23-4.17 (m, 2H), 3.90-3.86 (m, 2H), 3.81 (t, J=6.3 Hz, 2H), 3.76-3.72 (m, 2H), 3.68 (d, J=9.6 Hz, 6H), 3.46 (t, J=6.3 Hz, 2H), 3.30 (s, 6H).

$^{13}$C NMR (126 MHz, $CDCl_3$) d 152.60 (d, J=246.1 Hz), 146.92 (d, J=10.9 Hz), 131.90 (d, J=5.7 Hz), 122.61 (d,

J=3.6 Hz), 114.93 (d, J=4.0 Hz), 114.79, 102.20 (d, J=1.6 Hz), 71.31, 71.06, 70.80, 70.74, 70.65, 69.71, 69.21, 52.67, 30.44.

Example 8: 1-Bromo-4-[11-bromo-3,6,9-trioxaundecyloxy]-2-dimethoxymethyl-benzene (HDP 30.2643)

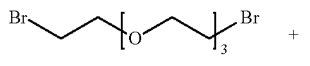

HDP 30.0381

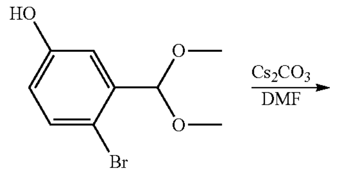

HDP 30.2631

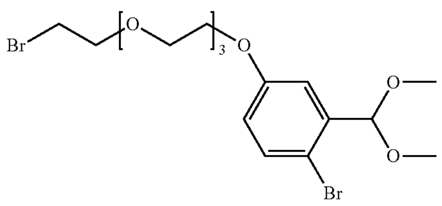

HDP 30.2643

By applying the procedure of example 5 on the crude product of example 4, 2.757 g (57%) title compound (HDP 30.2643) was achieved as an oil.

$^1$H NMR (500 MHz, $CDCl_3$) d 7.42 (d, J=8.7 Hz, 1H), 7.18 (d, J=3.2 Hz, 1H), 6.79 (dd, J=8.7, 3.1 Hz, 1H), 5.50 (s, 1H), 4.16-4.09 (m, 2H), 3.87-3.83 (m, 2H), 3.81 (t, J=6.3 Hz, 2H), 3.74-3.71 (m, 2H), 3.70-3.66 (m, 6H), 3.47 (t, J=6.3 Hz, 2H), 3.38 (s, 6H).

$^{13}$C NMR (126 MHz, CDCL3) d 158.22, 137.89, 133.57, 117.11, 114.31, 113.52, 102.99, 71.34, 70.99, 70.83, 70.77, 70.67, 69.77, 67.89, 54.08, 30.44.

MS ($ESI^+$) found.: 502.00/504.00/506.00;

calc. for $[M+NH_4]^+$: 502.04/504.04/506.04 ($C_{17}H_{30}Br_2NO_6$).

found.: 453.08/455.08/457.08;

calc. for $[MH-OMe]^+$: 452.99/454.99/456.99 ($C_{16}H_{23}Br_2O_5$).

Example 9: 1-[11-Fmoc-amino-3,6,9-trioxaundecyloxy]-4-dimethoxymethyl-benzene (HDP 30.2640)

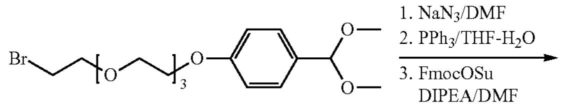

HDP 30.2637

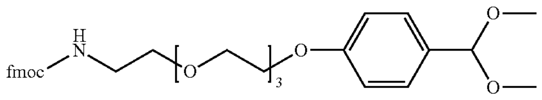

HDP 30.2640

The product from example 5, HDP 30.2637 (1.725 g, 4.24 mmol) was dissolved in 30 ml dry DMF, sodium azide 975 mg (12.7 mmol, 3 eq.) were added, and the suspension was stirred over night at ambient temperature. The solvent was then evaporated, the residue taken up in 50 ml tert-butylmethylether (MTBE) and washed with sodium bicarbonate and brine (50 ml each). The organic phase was dried over $MgSO_4$ and evaporated to a clear oil (1.435 g, yield 92%) containing the intermediate 1-[11-azido-3,6,9-trioxaundecyloxy]-4-dimethoxy¬methyl-benzene.

MS ($ESI^+$) found.: 392.25; calc. for $[M+Na]^+$: 392.18 ($C_{17}H_{27}N_3NaO_6$).

found.: 338.25; calc. for $[MH-OMe]^+$: 338.17 ($C_{16}H_{24}N_3O_5$).

The azide intermediate was then dissolved in THF and 2.038 mg (2 eq.) triphenylphosphine was added, followed by 2 ml water. The mixture was stirred overnight at room temperature until cessation of gas evolution. After 21 h the volatiles were evaporated and the remaining mixture of phosphins and intermediate 1-[11-amino-3,6,9-trioxaundecyloxy]-4-dimethoxy¬methyl-benzene was dissolved in 20 ml DMF.

Fmoc-N-hydroxysuccinimidester 1.57 g (1.2 eq.) and N-ethyldiisopropylamine (1320 µl; 2 eq) were added. After stirring at room temperature for 17 h additional 785 mg Fmoc-OSu were added. After complete conversion of intermediate amine, the solvent was evaporated and the residue was dissolved in 100 ml dichloromethane, washed with water (2×100 ml) and brine (100 ml), dried ($MgSO_4$) and reduced to dryness. The crude product was purified on silica gel with a gradient of 0 to 100% MTBE in n-hexane to yield 617 mg (28%) title compound as a viscous oil.

$^1$H NMR (500 MHz, $CDCl_3$) d 7.75 (dt, J=7.6, 0.9 Hz, 2H), 7.60 (d, J=7.5 Hz, 2H), 7.39 (tt, J=7.4, 0.9 Hz, 2H), 7.35-7.28 (m, 4H), 6.90-6.84 (m, 2H), 5.42 (t, J=5.7 Hz, 1H), 5.33 (s, 1H), 4.40 (d, J=6.9 Hz, 2H), 4.21 (t, J=6.9 Hz, 1H), 4.08 (t, J=4.9 Hz, 2H), 3.80 (t, J=4.9 Hz, 2H), 3.72-3.58 (m, 8H), 3.55 (t, J=5.1 Hz, 2H), 3.37 (q, J=5.4 Hz, 2H), 3.29 (s, 6H).

$^{13}$C NMR (126 MHz, $CDCl_3$) d 158.77, 156.47, 143.97, 141.26, 127.84, 127.69, 127.60, 126.98, 125.02, 119.90, 114.14, 102.95, 70.79, 70.55, 70.30, 69.99, 69.85, 69.67, 67.32, 66.44, 52.55, 47.24, 40.90.

MS ($ESI^+$) found.: 588.33; calc. for $[M+Na]^+$: 588.26 ($C_{32}H_{39}NNaO_8$).

found.: 534.33; calc. for $[MH-OMe]^+$: 534.25 ($C_{31}H_{36}NO_7$).

Example 10: 1-[11-Fmoc-amino-3,6,9-trioxaundecyloxy]-3-dimethoxymethyl-benzene (HDP 30.2650)

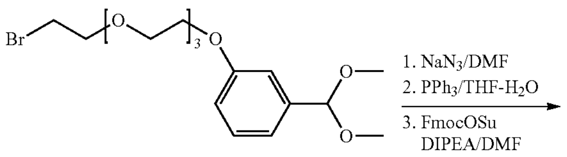

HDP 30.2641

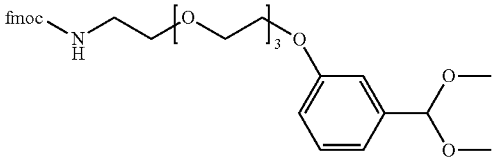

HDP 30.2650

By applying the procedure of example 9 on 1.082 g crude product of example 6, 106 mg (7%) title compound (HDP 30.2650) was achieved as an oil.

MS ($ESI^+$) found.: 588.33; calc. for $[M+Na]^+$: 588.26 ($C_{32}H_{39}NNaO_8$).

Example 11: 1-(11-Fmoc-amino-3,6,6-trioxaun-decyl)-4-dimethoxymethyl-2-fluoro-benzene (HDP 30.2651)

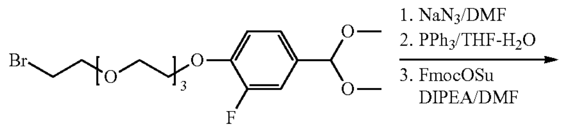

HDP 30.2642

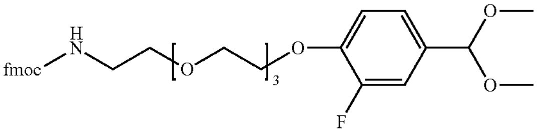

HDP 30.2651

By applying the procedure of example 9 on 1.900 g crude product of example 7, 112 mg (4%) title compound (HDP 30.2651) was achieved as an oil.

MS ($ESI^+$) found.: 606.33; calc. for $[M+Na]^+$: 606.25 ($C_{32}H_{38}FNNaO_8$).

found.: 552.33; calc. for $[MH-OMe]^+$: 552.24 ($C_{31}H_{35}FNO_7$).

Example 12: 1-Bromo-4-[11-Fmoc-amino-3,6,9-trioxaundecyloxy]-2-dimethoxymethyl-benzene (HDP 30.2652)

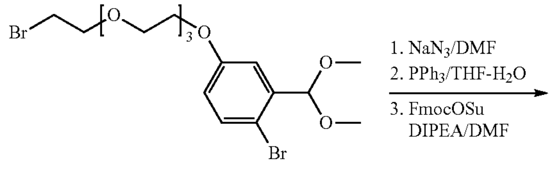

HDP 30.2643

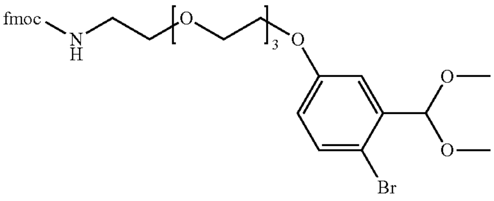

HDP 30.2652

By applying the procedure of example 9 on 2.625 g g crude product of example 8, 193 mg (6%) title compound (HDP 30.2652) was achieved as an oil.

MS ($ESI^+$) found.: 666.17/668.17.

calc. for $[M+Na]^+$: 666.17/668.17 ($C_{32}H_{38}BrNNaO_8$).

Example 13: Fmoc-Val-Ala-PAP-CHO (HDP 30.2623)

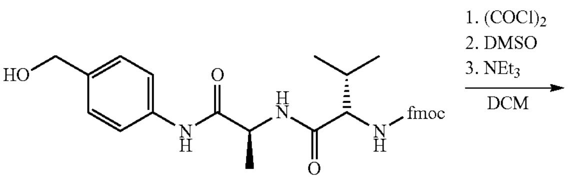

HDP 30.1419

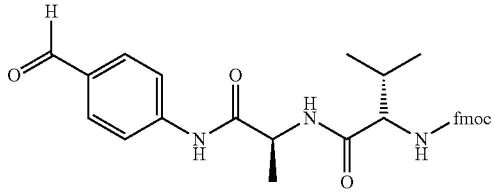

HDP 30.2623

In a three-necked flask, equipped with thermometer, dropping funnel and rubber septum, 20 ml dry dichloromethane was treated with (446 μl, 5.2 mmol) oxalyl chloride and the solution was cooled to −80° C. under argon atmosphere.

DMSO (739 μl, 10.4 mmol) was added dropwise by a syringe via the rubber septum, maintaining the temperature below −70° C. After stirring for 15 min Fmoc-Val-Ala-PAB-OH (HDP 30.1419, 2.062 g, 4.0 mmol) dissolved in 20 ml dichloromethane was added dropwise through the dropping funnel over a period of 30 min and the mixture was stirred for another 30 min.

Subsequently triethylamine (2.634 ml, 19.0 mmol) was added by a syringe and after 5 min the cooling bath was removed and reaction was allowed to warmup to room temperature. Then 25 ml water and 25 ml dichloromethane were added and the phases were separated. The aqueous phase was extracted with 20 ml dichloromethane and the combined organic phases were washed with 20 ml 0.2M citric acid, 3×20 ml water and 20 ml brine. After drying ($MgSO_4$) the solvent was evaporated and the crude product (965 mg) was purified on silica gel with a gradient of 0-20% ethyl acetate in dichloromethane to yield 631 mg (31%) product as an amorphous solid.

$^1H$ NMR (500 MHz, $D_6$-DMSO) d 10.36 (s, 1H), 9.89 (s, 1H), 8.22 (d, J=6.8 Hz, 1H), 7.91-7.79 (m, 6H), 7.74 (t, J=8.6 Hz, 2H), 7.45-7.29 (m, 5H), 4.47 (p, J=7.0 Hz, 1H), 4.37-4.28 (m, 1H), 4.28-4.19 (m, 2H), 3.95 (dd, J=8.9, 7.0 Hz, 1H), 2.02 (h, J=6.7 Hz, 1H), 1.35 (d, J=7.1 Hz, 3H), 0.92 (d, J=6.7 Hz, 3H), 0.88 (d, J=6.7 Hz, 3H).

$^{13}C$ NMR (126 MHz, $D_6$-DMSO) d 191.35, 171.75, 171.03, 156.05, 144.40, 143.79, 143.69, 140.61, 131.30, 130.68, 127.52, 127.50, 126.93, 125.22, 119.96, 119.95, 118.76, 65.63, 59.86, 49.20, 46.64, 30.32, 19.06, 18.12, 17.70.

MS ($ESI^+$) found.: 536.25 calc. for $[M+Na]^+$: 536.22 ($C_{30}H_{31}N_3NaO_5$).

Example 14: Fmoc-Val-Ala-PAP-CH(OMe)$_2$ (HDP 30.2677)

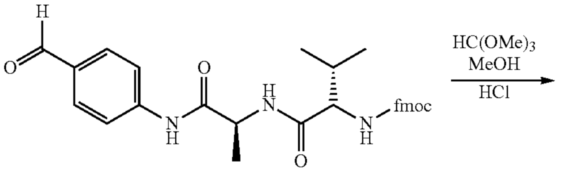

HDP 30.2623

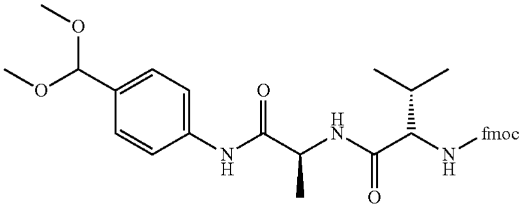

HDP 30.2677

Step 13 product HDP 30.2623 (514 mg, 1.00 mmol) was dissolved in 20 ml methanol. Triemethyl orthoformate (5.47 ml, 50 mmol) and 4-toluenesulfonic acid monohydrate (21 mg, 0.1 mmol) and 20 ml dichloromethane was added and the mixture was refluxed under argon atmosphere. After 5 h more trimethyl orthoformate (5.47 ml) and 4-toluenesulfonic acid (210 mg) was added and heating was continued for additional 2 h. The reaction mixture was cooled and purred into 50 ml saturated sodium bicarbonate with vigorous stirring. After cessation of gas evolution 100 ml dichloromethane was added and the turbid mixture was centrifuged at 4000×g in 40 ml portions. The clear upper layer was removed and the organic layers were washed with 15 ml water, followed by centrifugation. The combined organics were evaporated and the residue was co-evaporated with 2×20 ml methanol to remove traces of water. The residue was taken up with 100 ml dichloromethane and insoluble material was filtered off. The filtrate was evaporated and the residue was triturated with 50 ml MTBE for 1 h at 40° C., then cooled to room temperature and filtered with suction. The precipitate washed with 20 ml MTBE and dried in vacuo to yield 445 mg (79%) title product as amorphous solid.

Example 15: Fmoc-Val-Ala-OAB-OH (HDP 30.2761)

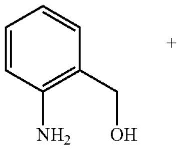

2-Amino-benzyl alcohol

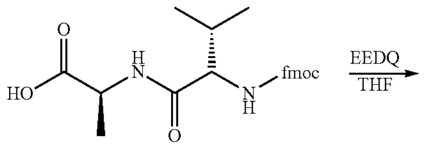

HDP 30.1414

-continued

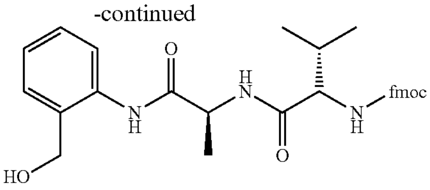

HDP 30.2761

Dipeptide Fmoc-Val-Ala-OH (4.105 g, 10.0 mol) and 4-Aminobenzyl alcohol (1.293 g, 1.05 eq.) were dissolved in 60 ml abs. tetrahydrofuran (THF). 2-Ethoxy-N-(ethoxycarbonyl)-1,2-dihydroquinoline (EEDQ, 2.597 g, 1.05 eq.) was added and the mixture was stirred at room temperature, protected from light.

After 3 days the reaction mixture that formed a gelatinous matter was diluted with 140 ml MTBE and stirred until a fine precipitate formed that was filtered off with suction washed with 50 ml MTBE and dried to 4.480 g (87%) title product HDP 30.2761 as colorless solid.

$^1$H NMR (500 MHz, D$_6$-DMSO) d 9.40 (s, 1H), 8.20 (d, J=7.0 Hz, 1H), 7.89 (d, J=7.5 Hz, 2H), 7.74 (t, J=7.6 Hz, 2H), 7.53 (d, J=8.0 Hz, 1H), 7.46-7.36 (m, 4H), 7.32 (tt, J=7.5, 1.3 Hz, 2H), 7.23 (td, J=7.6, 1.7 Hz, 1H), 7.15 (td, J=7.4, 1.3 Hz, 1H), 5.24 (t, J=5.6 Hz, 1H), 4.56-4.42 (m, 3H), 4.36-4.28 (m, 1H), 4.28-4.20 (m, 2H), 3.96 (dd, J=9.1, 6.8 Hz, 1H), 2.04 (h, J=6.8 Hz, 1H), 1.35 (d, J=7.1 Hz, 3H), 0.90 (d, J=6.7 Hz, 3H), 0.87 (d, J=6.8 Hz, 3H).

$^{13}$C NMR (126 MHz, D$_6$-DMSO) d 171.09, 170.90, 156.09, 143.83, 143.72, 140.65, 140.63, 135.08, 134.74, 127.55, 127.54, 127.23, 126.97, 126.87, 125.27, 124.64, 123.66, 120.00, 119.98, 65.65, 60.03, 59.86, 48.90, 46.65, 40.01, 39.84, 39.67, 39.50, 39.34, 39.17, 39.00, 31.23, 30.33, 19.15, 18.04, 17.89.

MS (ESI$^+$) found.: 538.25 calc. for [M+Na]$^+$: 538.23 ($C_{30}H_{33}N_3NaO_5$).

Example 16: Fmoc-Val-Ala-OAP-CH(OMe)2 (HDP 30.2769)

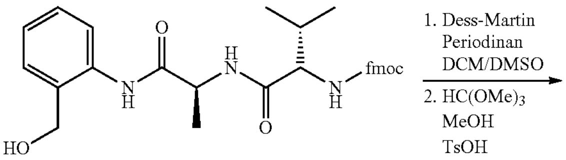

HDP 30.2761

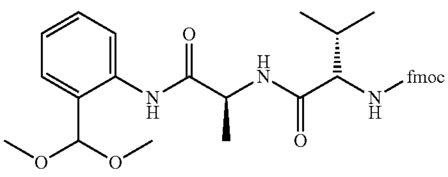

HDP 30.2769

To benzyl alcohol HDP 30.2761 from Step 15 (4.48 g, 8.69 mmol) 18 ml DMSO and 36 ml abs. dichloromethane followed by 3.66 g, 1.0 eq.) Dess-Martin periodinane, after stirring for 2 h, the resulted brownish solution was diluted with 90 ml chloroform and washed with 90 ml water. The aqueous phase was back extracted with 2×40 ml chloroform and the combined organics were washed shake with 90 ml saturated sodium bicarbonate until a pH of 7-8 was reached.

Then 30 ml 20% sodium thiosulfate solution was added and shaking was continued for 2 min. After separation the organic layer was washed with additional 90 ml water, dried ($MgSO_4$) and the volatiles were removed. The remaining 4.875 g was stirred with 150 ml MTBE until a fine precipitate formed that was filtered off with suction washed with 50 ml MTBE and dried to 4.307 g (97%) intermediate aldehyde as colorless solid.

MS ($ESI^+$) found.: 536.25 calc. for $[M+Na]^+$: 536.22 ($C_{30}H_{31}N_3NaO_5$).

4.187 g (8.152 mmol) of the aldehyde Fmoc-Val-Ala-OAP-CHO was then suspended in 80 ml methanol, trimethyl orthoformate (45 ml, 50 eq,) and 4-toluenesulfonic acid monohydrate (1.551 g, 1 eq.) were added and the mixture refluxed for 1 h under argon atmosphere. After cooling to room temperature, the reaction mixture into 100 ml saturated sodium bicarbonate with vigorous stirring.

100 ml chloroform was added to dissolve the gelatinous mater and the phases were separated. The aqueous phase was back extracted with 2×50 ml chloroform and the combined organic layers were washed with 50 ml half-saturated brine, dried ($MgSO_4$) and evaporated. The crude product was purified on silica gel with a gradient of 0 to 20% ethyl acetate in dichloromethane to yield in 3.279 g (72%) title product HDP 30.2769 as an amorphous solid.

$^1$H NMR (500 MHz, $D_6$-DMSO) d 9.27 (s, 1H), 8.30 (d, J=7.0 Hz, 1H), 7.89 (d, J=7.5 Hz, 2H), 7.75 (t, J=7.2 Hz, 2H), 7.70 (d, J=8.1 Hz, 1H), 7.48-7.38 (m, 4H), 7.32 (ddd, J=8.7, 6.7, 1.4 Hz, 3H), 7.18 (td, J=7.6, 1.3 Hz, 1H), 5.45 (s, 1H), 4.46 (p, J=7.0 Hz, 1H), 4.37-4.29 (m, 1H), 4.28-4.20 (m, 2H), 3.99 (dd, J=9.2, 6.8 Hz, 1H), 3.26 (s, 3H), 3.26 (s, 3H), 2.05 (h, J=6.7 Hz, 1H), 1.35 (d, J=7.1 Hz, 3H), 0.89 (d, J=6.8 Hz, 3H), 0.87 (d, J=6.7 Hz, 3H).

$^{13}$C NMR (126 MHz, $D_6$-DMSO) d 176.52, 176.05, 161.32, 149.06, 148.95, 145.89, 145.87, 140.68, 134.89, 133.97, 132.82, 132.80, 132.38, 132.23, 130.56, 130.55, 129.58, 129.11, 125.27, 106.40, 70.84, 65.01, 58.68, 58.37, 54.27, 51.85, 35.65, 24.41, 23.26, 22.69.

MS ($ESI^+$) found.: 582.33 calc. for $[M+Na]^+$: 582.26 ($C_{32}H_{37}N_3NaO_6$).

Example 17: BMP-Val-Ala-OAP-CH(OMe)$_2$ (HDP 30.2776)

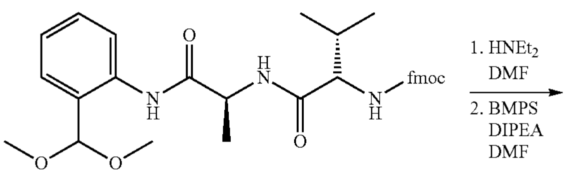

HDP 30.2769

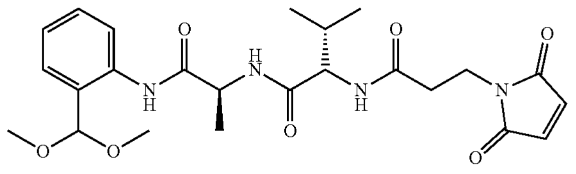

HDP 30.2776

Product from example 16, HDP 30.2769 (3.236 g, 5.782 mmol) was suspended in 30 ml DMF. Diethylamine (8 ml) was added and stirred for 30 min at room temperature to form a clear solution. The volatiles were evaporated and the residue was coevaporated with 30 ml fresh DMF and dried afterwards in high vacuum. The crude product contains the intermediate amine H-Val-Ala-OAP-CH(OMe)$_2$ and was used without further purification.

MS ($ESI^+$) found.: 360.25 calc. for $[M+Na]^+$: 360.19 ($C_{17}H_{27}N_3NaO_4$).

Intermediate free amine was dissolved in 30 ml DMF and 1.539 g (1 eq.) 3-(maleimido)propionic acid N-hydroxysuccinimide ester (BMPS) and 1.967 ml (2 eq.) N-ethyldiisopropylamine (DIPEA) were added and the solution was stirred for 1 h. The solvent was evaporated and the residue was stirred with 100 ml MTBE. The fine precipitate formed, was filtered off, washed with MTBE (20 ml) and dried in vacuo. The crude product was purified on silica gel with a gradient of 0 to 10% methanol in dichloromethane to yield 2.164 g (77%) pure title product as colorless amorphous solid.

$^1$H NMR (500 MHz, $D_6$-DMSO) d 9.20 (s, 1H), 8.27 (d, J=6.8 Hz, 1H), 8.00 (d, J=9.0 Hz, 1H), 7.69 (d, J=7.5 Hz, 1H), 7.43 (dd, J=7.7, 1.6 Hz, 1H), 7.33 (td, J=7.8, 1.7 Hz, 1H), 7.16 (td, J=7.5, 1.3 Hz, 1H), 6.99 (s, 2H), 5.44 (s, 1H), 4.41 (p, J=7.1 Hz, 1H), 4.22 (dd, J=8.8, 6.6 Hz, 1H), 3.61 (dq, J=17.1, 6.6 Hz, 2H), 3.27 (s, 3H), 3.26 (s, 3H), 2.48-2.40 (m, 2H), 2.01 (dh, J=20.3, 6.8 Hz, 1H), 1.33 (d, J=7.2 Hz, 3H), 0.84 (d, J=6.8 Hz, 3H), 0.81 (d, J=6.8 Hz, 3H).

$^{13}$C NMR (126 MHz, $D_6$-DMSO) d 171.03, 170.78, 170.63, 169.50, 135.51, 134.47, 129.50, 128.70, 127.15, 124.23, 123.70, 101.33, 57.27, 53.46, 53.18, 49.08, 33.99, 33.64, 30.32, 19.10, 17.91, 17.28.1.

MS ($ESI^+$) found.: 511.25 calc. for $[M+Na]^+$: 511.22 ($C_{24}H_{32}N_4NaO_7$).

Example 18: Fmoc-Val-Ala-MAB-OH (HDP 30.2767)

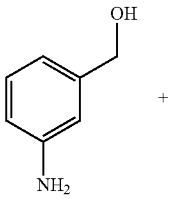

3-Amino-benzylalkohol

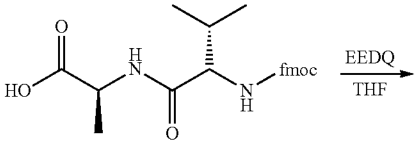

HDP 30.1414

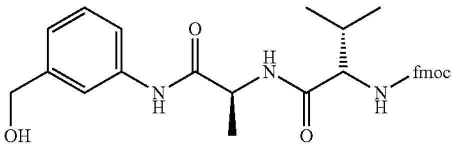

HDP 30.2767

By performing the procedure of example 15 with the 3-aminobenzyl alcohol, 4.698 g (91%) of the title product HDP 30.2767 g was achieved as an amorphous solid.

$^1$H NMR (500 MHz, $D_6$-DMSO) d 9.95 (s, 1H), 8.17 (d, J=7.0 Hz, 1H), 7.88 (d, J=7.5 Hz, 2H), 7.75 (t, J=7.8 Hz, 2H), 7.59 (d, J=1.9 Hz, 1H), 7.50-7.37 (m, 4H), 7.32 (tt, J=7.5, 1.6 Hz, 2H), 7.24 (t, J=7.8 Hz, 1H), 6.99 (d, J=7.8 Hz, 1H), 5.19 (t, J=5.7 Hz, 1H), 4.45 (dd, J=14.7, 6.5 Hz, 3H), 4.36-4.28 (m, 1H), 4.28-4.19 (m, 2H), 3.93 (dd, J=9.0, 7.1 Hz, 1H), 2.01 (h, J=6.8 Hz, 1H), 1.32 (d, J=7.0 Hz, 3H), 0.91 (d, J=6.7 Hz, 3H), 0.87 (d, J=6.7 Hz, 3H).

$^{13}$C NMR (126 MHz, $D_6$-DMSO) d 170.93, 156.08, 143.80, 143.72, 143.16, 140.63, 140.62, 138.78, 128.29, 127.57, 127.54, 126.98, 125.29, 121.21, 120.02, 120.00, 117.41, 117.11, 65.63, 62.77, 59.92, 48.95, 46.61, 30.32, 19.13, 18.19, 18.07, 3.26.

MS (ESI$^+$) found.: 538.33 calc. for $[M+Na]^+$: 538.23 ($C_{30}H_{33}N_3NaO_5$).

Example 19: Fmoc-Val-Ala-MAP-CH(OMe)2 (HDP 30.2778)

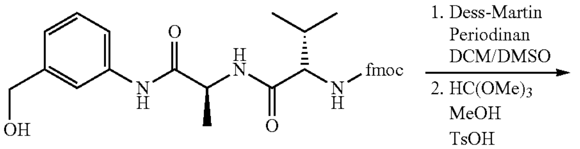

HDP 30.2767

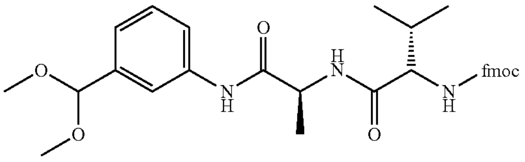

HDP 30.2778

By performing the procedure of example 16 with the compound of example 18 (HDP 30.2767), with omitting the final silica gel chromatography, 6.28 g crude title product HDP 30.2778 was achieved as an amorphous solid, that was pure enough to use it for the next step.

Example 20: BMP-Val-Ala-MAP-CH(OMe)$_2$ (HDP 30.2776)

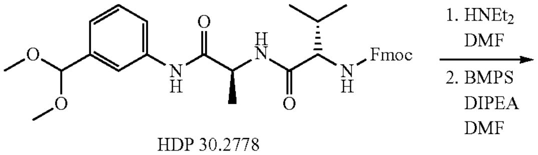

HDP 30.2778

-continued

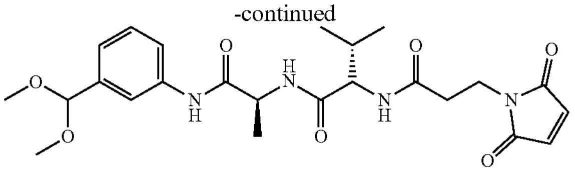

HDP 30.2781

By performing the procedure of example 17 with the compound of example 19 (HDP 30.2778), the title product HDP 30.2781 was achieved in 95% yield based on HDP 30.2767 as an amorphous solid.

$^1$H NMR (500 MHz, $D_6$-DMSO) d 9.89 (s, 1H), 8.16 (d, J=6.9 Hz, 1H), 8.02 (d, J=8.4 Hz, 1H), 7.66 (t, J=1.9 Hz, 1H), 7.64-7.54 (m, 1H), 7.30 (t, J=7.9 Hz, 1H), 7.06 (dt, J=7.6, 1.4 Hz, 1H), 7.00 (s, 2H), 5.35 (s, 1H), 4.38 (p, J=7.1 Hz, 1H), 4.14 (dd, J=8.4, 6.8 Hz, 1H), 3.68-3.57 (m, 2H), 3.24 (s, 6H), 2.50-2.40 (m, 2H), 2.00-1.90 (m, J=6.8 Hz, 1H), 1.32 (d, J=7.1 Hz, 3H), 0.87 (d, J=6.8 Hz, 3H), 0.83 (d, J=6.8 Hz, 3H).

$^{13}$C NMR (126 MHz, $D_6$-DMSO) d 171.09, 170.77, 170.71, 169.76, 138.90, 138.79, 134.52, 128.46, 121.42, 118.99, 117.25, 102.42, 57.71, 52.44, 52.42, 49.08, 34.02, 33.70, 30.26, 19.11, 18.17, 17.83.

MS (ESI$^+$) found.: 511.25 calc. for $[M+Na]^+$: 511.22 ($C_{24}H_{32}N_4NaO_7$).

General Procedure A for Cyclic Acetales

To a solution of diol compound in dry DMF (100 μl/mg), dimethyl acetal compound (10 eq.) was added. The mixture was acidified with trifluoroacetic acid (10 μl/mg) and stirred for at ambient temperature under argon atmosphere until a clear solution has formed. Subsequently the solvent was evaporated in high vacuum and the remaining was re-dissolved in fresh DMF. A sample was quenched in 1% triethylamine in methanol and analyzed by HPLC to show complete conversion of starting material.

DMF solution was dripped into the 10-fold volume of an ice-cooled solution of 0.1% triethylamine in tert-butylmethyl ether (MTBE) and the resulted precipitate was isolated by centrifugation. The supernatant was discharged and the pellet was re-suspended in the same volume of 0.1% triethylamine MTBE and centrifuged again. The vacuum dried crude product was further purified by prep.-HPLC.

General Procedure B for Cyclic Acetales

Diol compound (1 eq.) and dimethyl acetal compound (8 eq.) were placed into a centrifugal tube and dissolved in DMF/TFA 4:1 (v/v, 20 μl/μmol diol compound). The tube was shaken at room temperature until HPLC control indicated complete conversion of diol compound (1-18 h). Then the 20-fold volume of ice-cooled MTBE was added and the precipitate was isolated by centrifugation. The first pellet was resuspended in the same volume of MTBE containing 2 vol-% triethylamine and centrifuged again. The dried pellet was used for the next reaction without further purification.

Example 21: α-Amanitin-(Fmoc-Val-Ala-4-amino-benzylidenacetal) HDP 30.2681

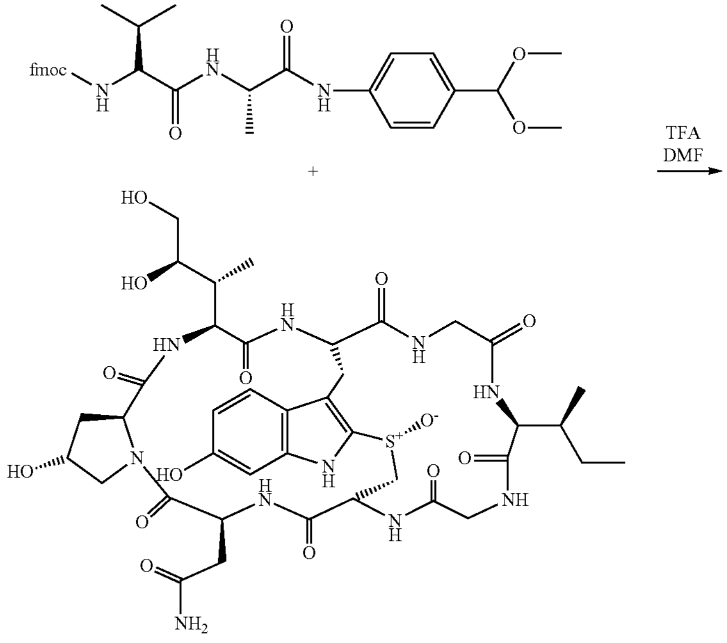

HDP 30.2677 + α-amanitin

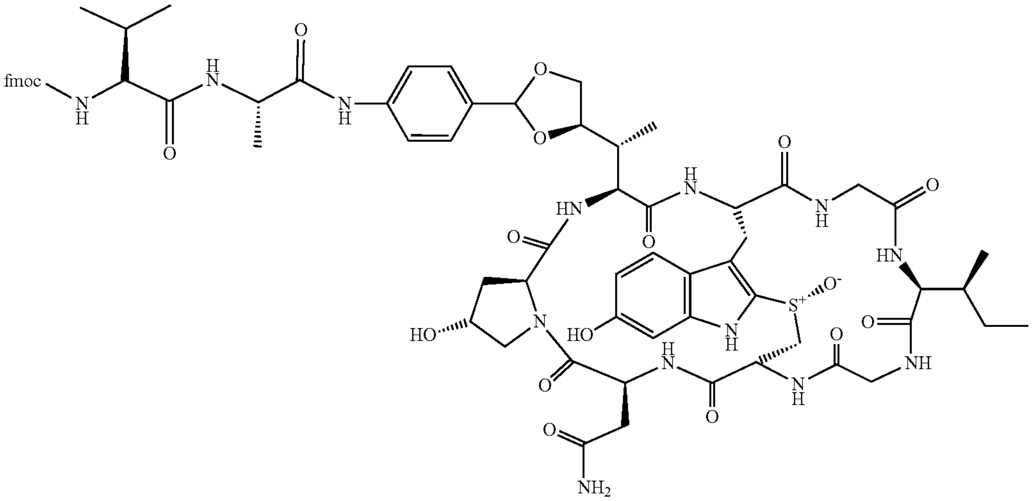

HDP 30.2681

Alpha-Amanitin (30.98 mg) and HDP 30.2677 was reacted according to general procedure A. Crude product was purified on Phenomenex Luna-C18(2), 10 μm, 250×21.2 mm with a gradient from 5 to 100% acetonitrile in water in 15 min. Product containing fraction from 10.40-11.08 min was freeze-dried to yield 37.07 mg (78%) lyophilizate.

MS ($ESI^+$) found.: 1414.67; calc. for $[MH]^+$:1414.58 ($C_{69}H_{84}N_{13}O_{18}S$).

Example 22: α-Amanitin-[4-(11-Fmoc-amino-3,6,9-trioxaundecyloxy)-benzylidenacetal] HDP 30.2665
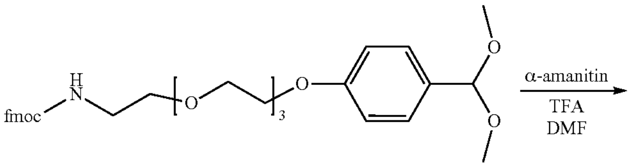
HDP 30.2640
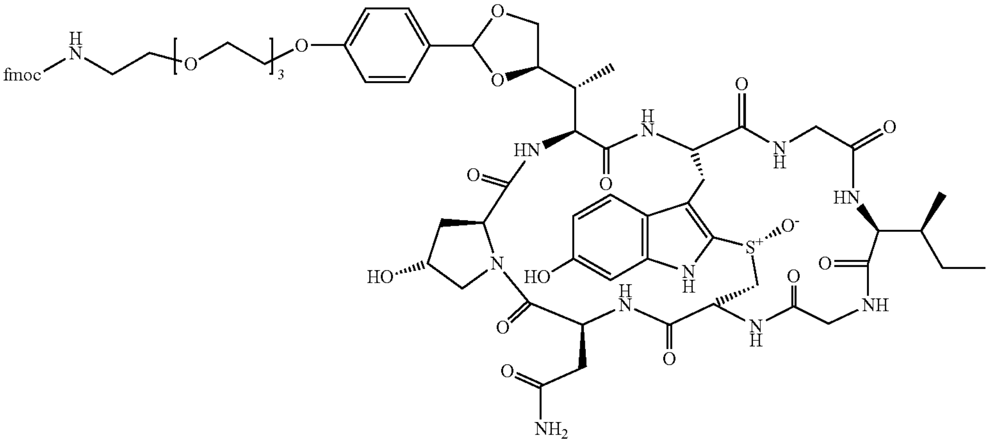
HDP 30.2665
According to general procedure A, α-amanitin (20.51 mg) and HDP 30.2640 from example 9 was reacted to yield 20.96 mg (65%) title product as lyophilized powder.
Example 23: α-Amanitin-[3-(11-Fmoc-amino-3,6,9-trioxaundecyloxy)-benzylidenacetal] HDP 30.2666
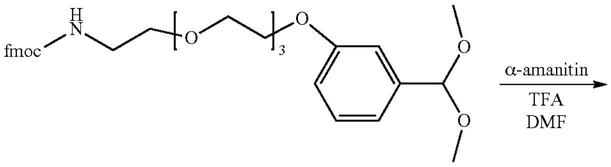
HDP 30.2650
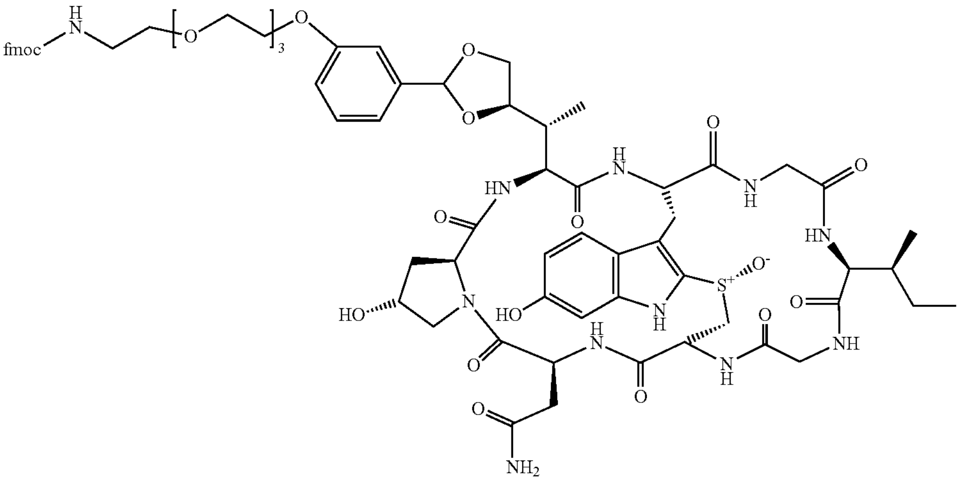
HDP 30.2666

According to general procedure B, α-amanitin (20.51 mg) and HDP 30.2650 from example 10 was reacted and the crude title compound was used further without purification.

Example 24: α-Amanitin-[4-(11-Fmoc-amino-3,6,9-trioxaundecyloxy)-3-fluoro-benzylidenacetal] HDP 30.2667

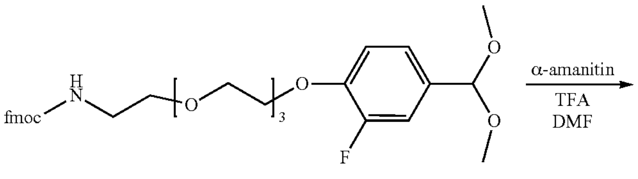

HDP 30.2651

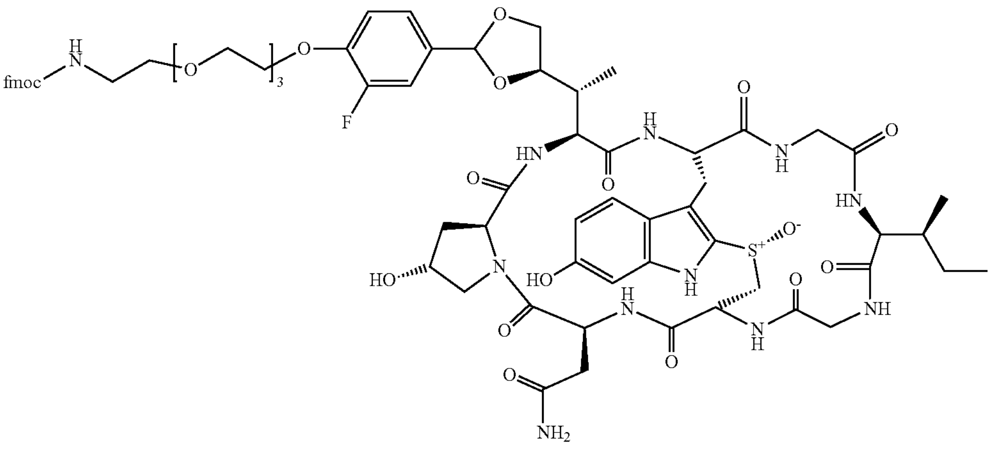

HDP 30.2667

According to general procedure B, α-amanitin (20.51 mg) and HDP 30.2651 from example 11 was reacted and the crude title compound was used further without purification.

Example 25: α-Amanitin-[2-bromo-3-(11-Fmoc-amino-3,6,9-trioxaundecyloxy)-benzylidenacetal] HDP 30.2668

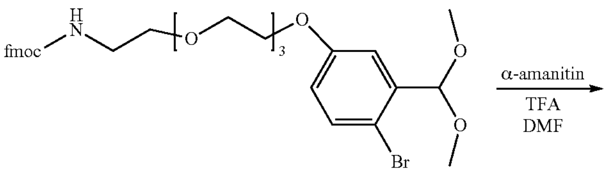

HDP 30.2652

-continued
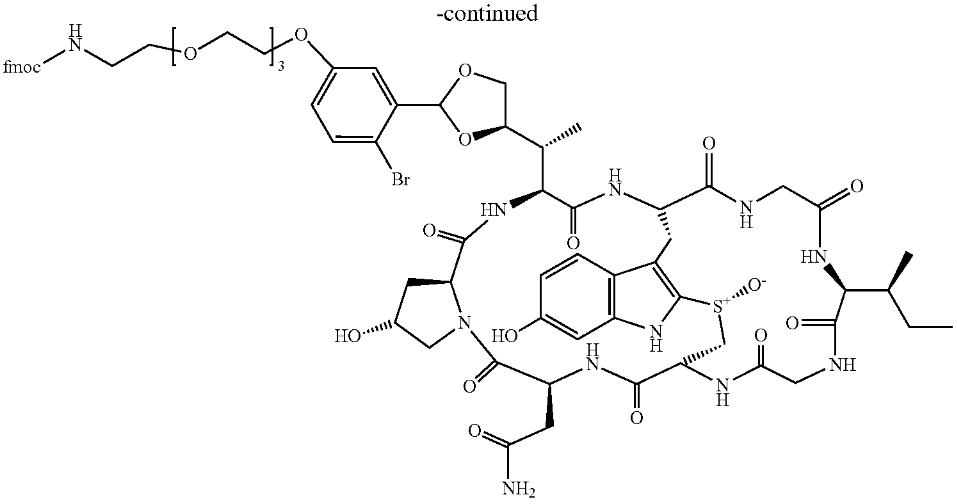
HDP 30.2668
According to general procedure B, α-amanitin (20.51 mg) and HDP 30.2652 from example 11 was reacted and the crude title compound was used further without purification.
Example 26: α-Amanitin-(BMP-Val-Ala-4-amino-benzylidenacetal) HDP 30.2684
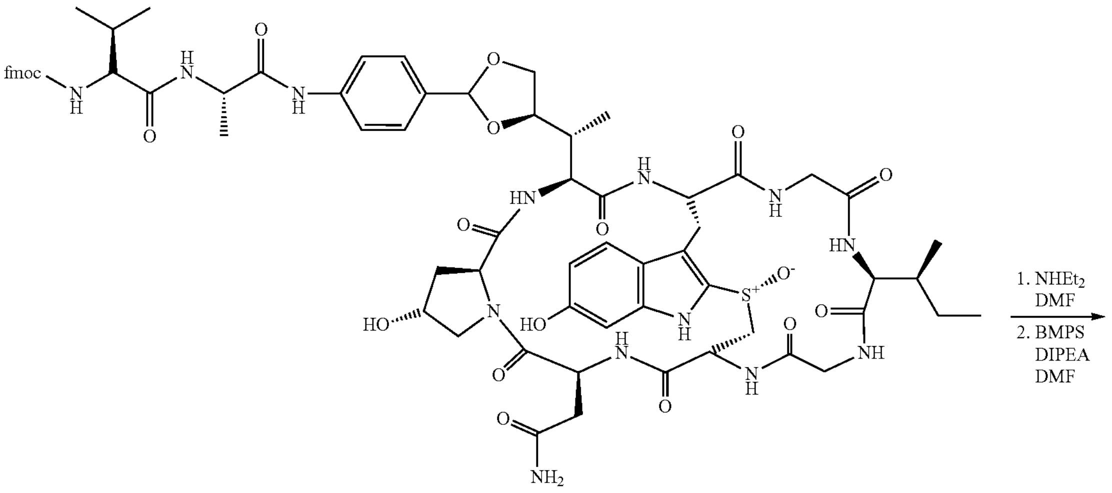
HDP 30.2681

-continued

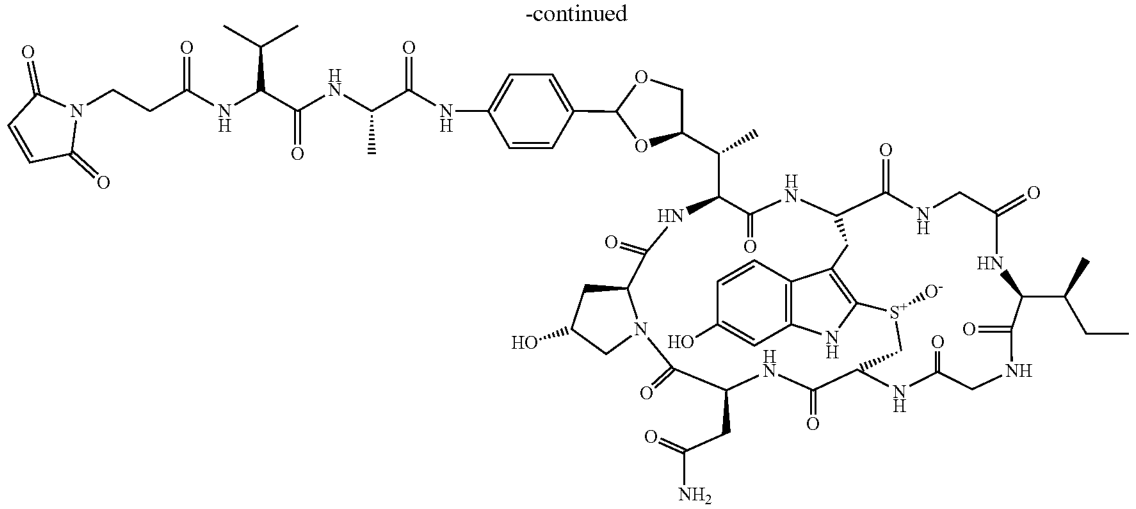

HDP 30.2684

Cyclic acetal HDP 30.2681 (37.07 mg, 26.21 μmol) was dissolved in 2 ml dry DMF. Diethylamine (92 μl, 891 μmol) was added and the mixture was stirred 15 min at ambient temperature. The volatiles were evaporated in vacuo and the residue was re-dissolved in dry DMF. HPLC and MS analysis showed complete deprotection to the free amine.

(MS-ESI$^+$) found.: 1192.67; calc. for $[MH]^+$: 1192.51 ($C_{54}H_{74}N_{13}O_{16}S$).

3-(Maleimido)propionic acid N-hydroxysuccinimide ester (BMPS, 14 mg, 52.42 μmol=2 eq.) dissolved in 500 μl dry DMF was added followed by 8.92 μl (52.42 μmol=2 eq) N,N-diisopropylethylamine. After stirring at room temperature for 2 h the reaction mixture was dripped into 10 ml ice cooled MTBE and the precipitate was isolated by centrifugation. The crude pellet was purified by prep. HPLC on Luna-C18(2) with a gradient of 5-50% acetonitrile in water in 15 min. Product fraction from 11.9-12.8 min was freeze-dried to yield 20.85 mg (59%) colorless lyophilizate.

MS (ESI$^+$) found.: 1343.58; calc. for $[NM]^+$: 1343.54 ($C_{61}H_{79}N_{14}O_{19}S$).

Example 27: α-Amanitin-[4-(11-(3-maleimidopropyl-amido)-3,6,9-trioxaundecyloxy)-benzylidenacetal] HDP 30.2669

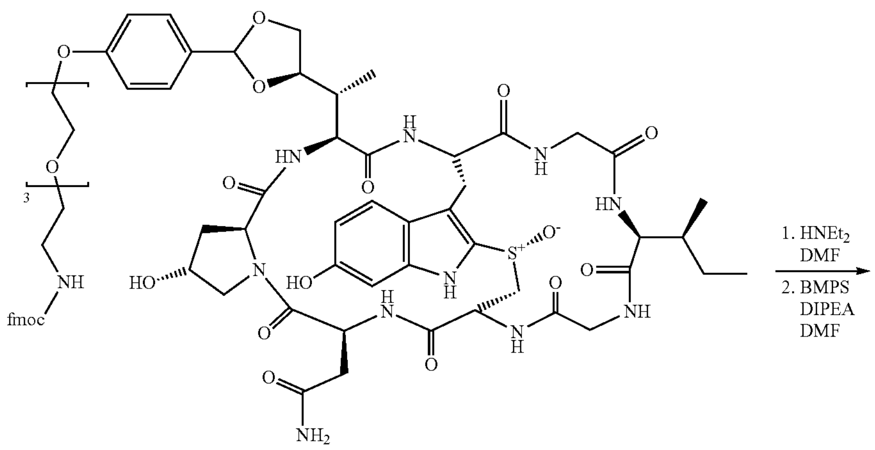

HDP 30.2665

-continued
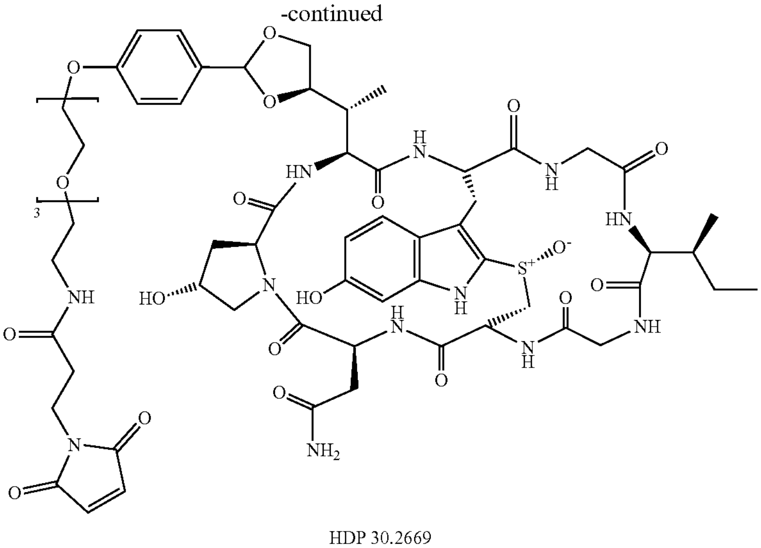
HDP 30.2669
By applying the procedure from example 26 on 20.96 mg HDP 30.2665 from example 22, the title product HDP 30.2669 (13.00 mg, 65%) was achieved as lyophilized powder.
MS ($ESI^+$) found.: 1371.58; calc. for $[NM]^+$: 1371.52 ($C_{61}H_{80}N_{12}NaO_{21}S$)).
Example 28: ca-Amanitin-[3-(11-(3-maleimidopropyl-amido)-3,6,9-trioxaundecyloxy)-benzylidenacetal] HDP 30.2670
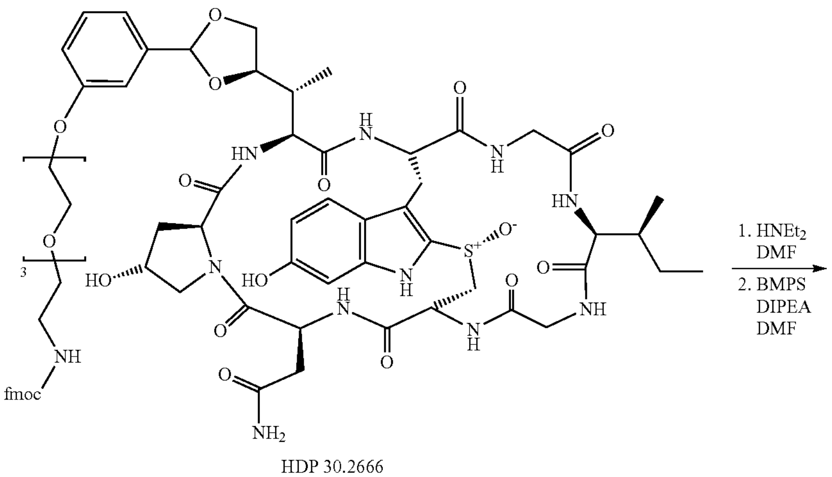
HDP 30.2666

-continued
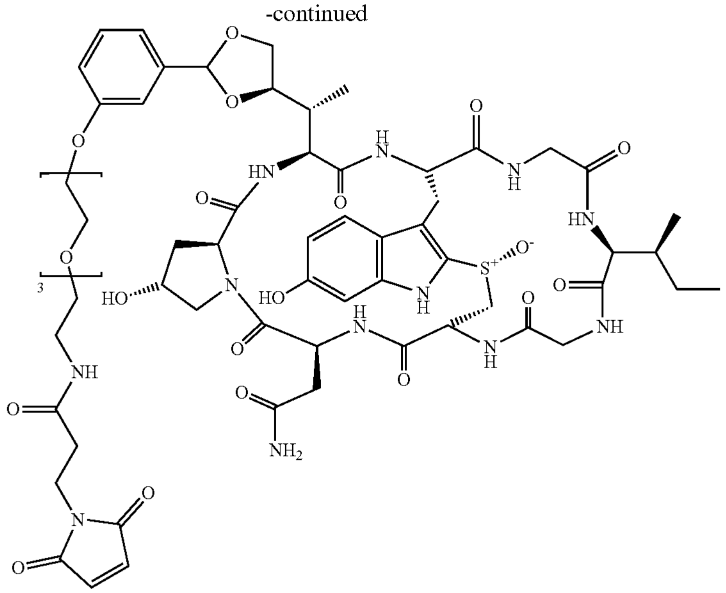
HDP 30.2670
By applying the procedure from example 26 on the crude HDP 30.2666 from example 23, the title product HDP 30.2670 (4.39 mg, 15% based on α-amanitin) was achieved as lyophilized powder.
MS ($ESI^+$) found.: 1371.50; calc. for $[NM]^+$: 1371.52 ($C_{61}H_{80}N_{12}NaO_{21}S$)).
Example 29: α-Amanitin-[4-(11-(3-maleimidopropyl-amido)-3,6,9-trioxaundecyloxy)-3-fluoro-benzylidenacetal] HDP 30.2671
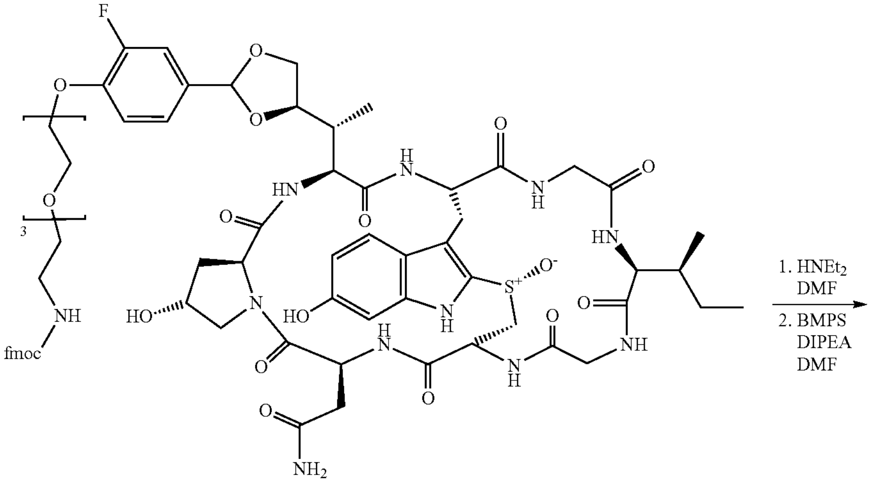
HDP 30.2667

-continued
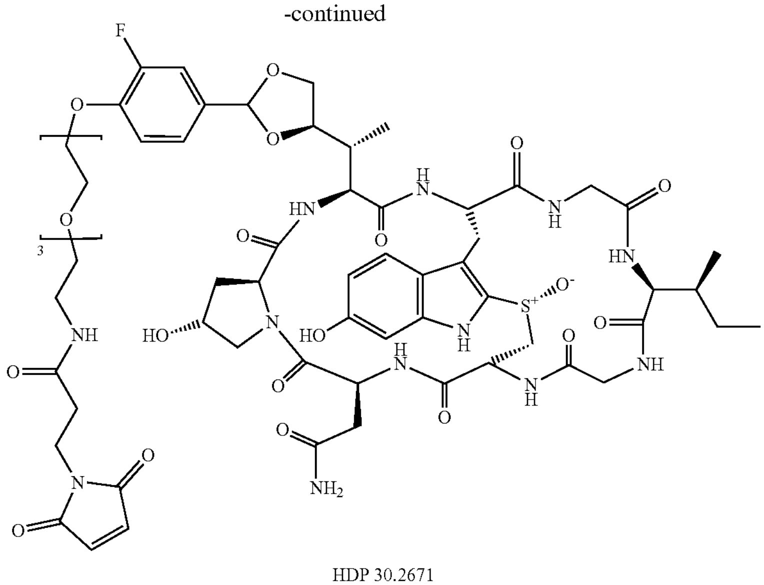
HDP 30.2671
By applying the procedure from example 26 on the crude HDP 30.2667 from example 24, the title product HDP 30.2671 (5.82 mg, 19% based on α-amanitin) was achieved as lyophilized powder.
MS ($ESI^+$) found.: 1389.50; calc. for $[NM]^+$: 1389.51 ($C_{61}H_{79}FN_{12}NaO_{21}S$).
Example 30: α-Amanitin-[2-bromo-3-(11-(3-maleimidopropyl-amido)-3,6,9-trioxaundecyloxy)-benzylidenacetal] HDP 30.2672
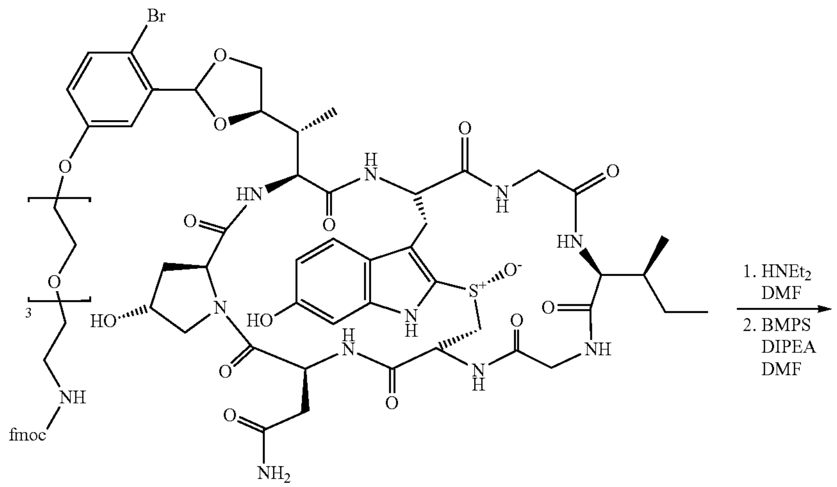
HDP 30.2668

-continued
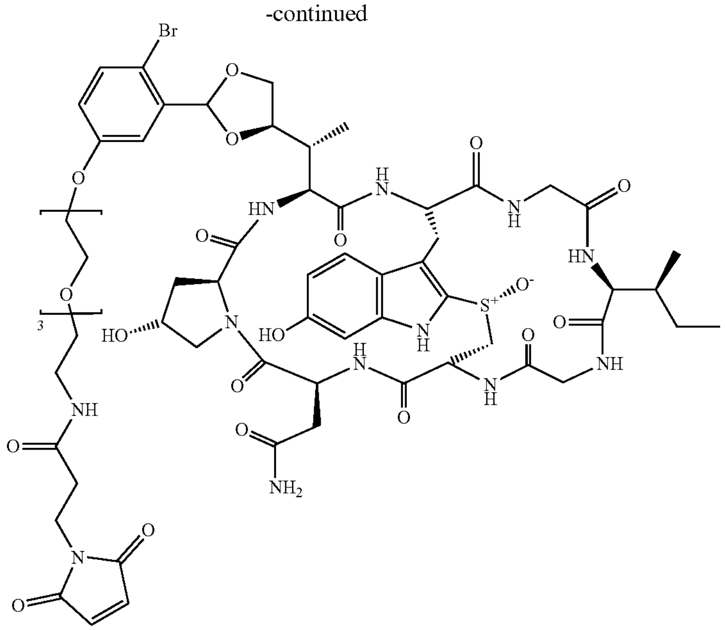
HDP 30.2672
By applying the procedure from example 26 on the crude HDP 30.2668 from example 24, the title product HDP 30.2672 (2.43 mg, 8% based on α-amanitin) was achieved as lyophilized powder.
MS ($ESI^+$) found.: 1449.42/1451.42;
calc. for $[NM]^+$: 1449.43/1451.43 ($C_{61}H_{79}BrN_{12}NaO_{21}S$).
Example 31: α-Amanitin-(BMP-Val-Ala-2-amino-benzylidenacetal) HDP 30.2792
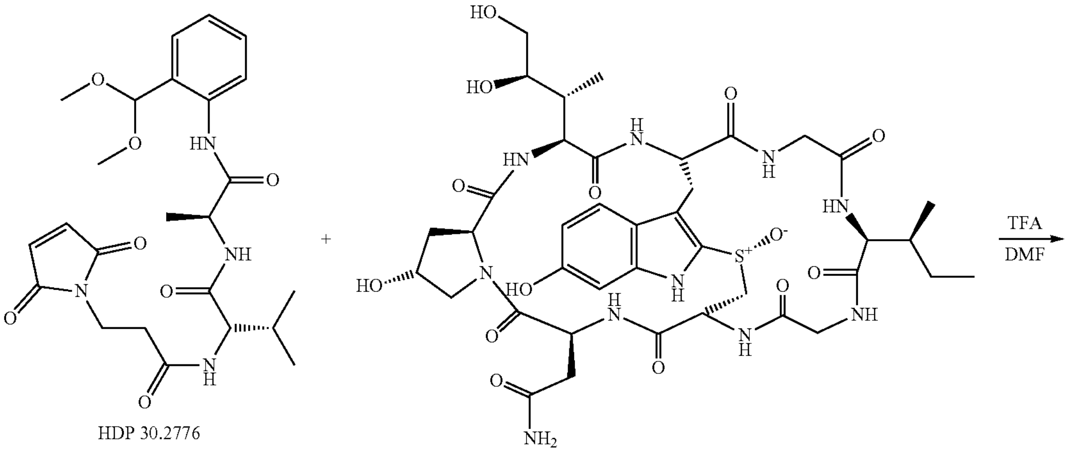
HDP 30.2776
α-amanitin -continued
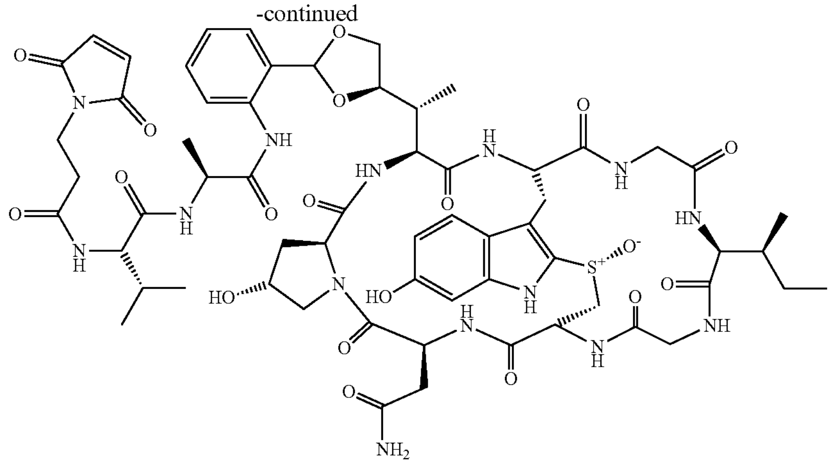
HDP 30.2792
The title compound could be prepared by reacting α-amanitin with compound HDP 30.2776 from example 17.
Example 32: α-Amanitin-(BMP-Val-Ala-3-amino-benzylidenacetal) HDP 30.2793
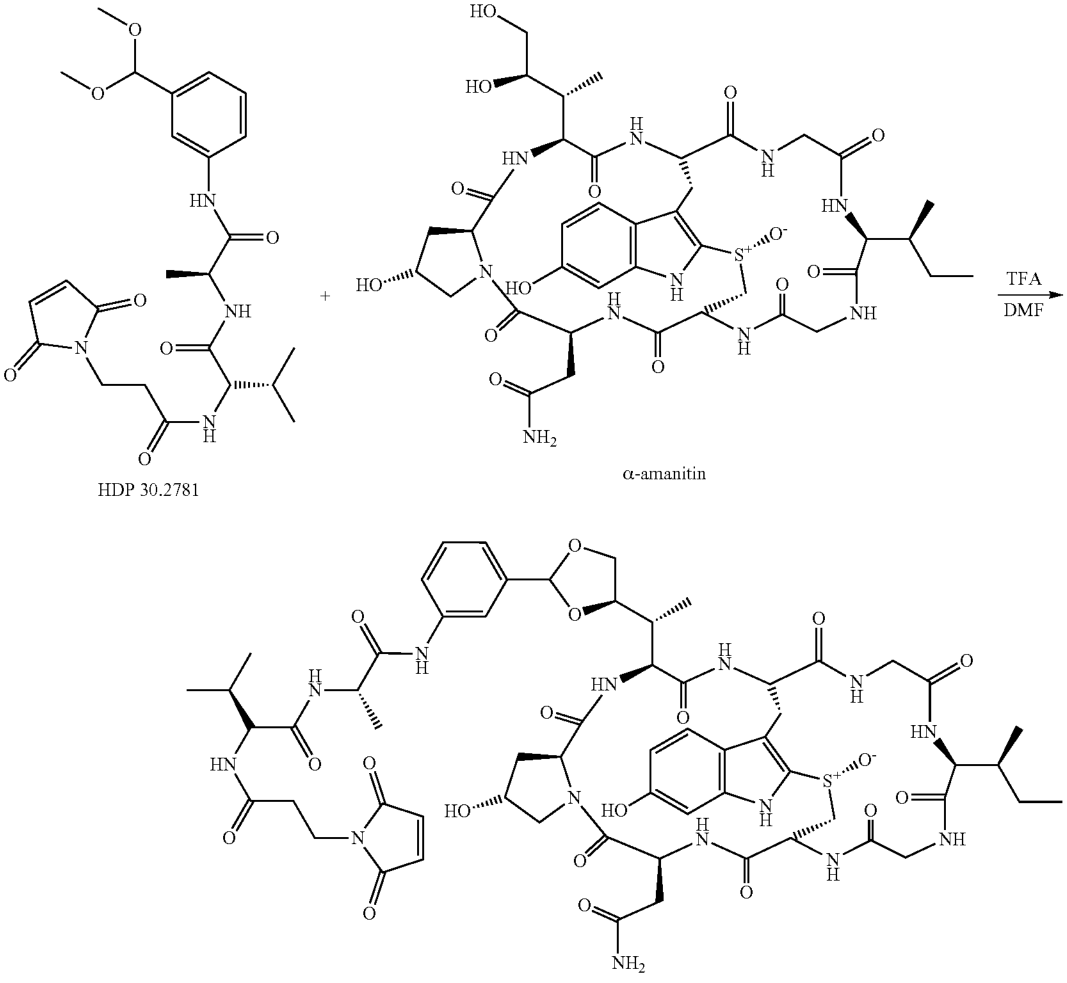
HDP 30.2781
α-amanitin
HDP 30.2793

The title compound could be prepared by reacting α-amanitin with compound HDP 30.2781 from example 20.

Example 33: Synthesis of Amatoxin Antibody Conjugates

A derivative of Trastuzumab, an Anti-Her2neu-specific antibody, with a D265C mutation ("Thiomab", aspartic acid to cysteine mutation at amino acid position 265 of the Ig heavy chain) was conjugated to the amatoxin-linker derivatives HDP 30.2669, HDP 30.2670, HDP 30.2671, HDP 30.2672 and HDP 30.2684.

For each conjugation reaction, 10 mg of the Thiomab in PBS buffer adjusted to 1 mM EDTA was be used. Cysteines were uncapped by reaction of antibody with 40 eq. TCEP for 3 h at 37° C. on a shaker and two consecutive dialyses at 4° C. in 1×PBS, 1 mM EDTA, pH 7.4 in a Slide-A-Lyzer Dialysis Cassette. Oxidation was performed by incubation of antibody with 20 eq. dehydroascorbic acid (dhAA) for 3 h at RT on a shaker.

Conjugation with the amatoxin-linker derivatives using 4 eq. HDP 30.2669, HDP 30.2670, HDP 30.2671, HDP 30.2672 and HDP 30.2684, respectively, solubilized in DMSO was done by incubation for 1 h at room temperature, and quenching by addition of 25 eq. N-acetyl-L-cysteine and incubation for 15 min at RT or overnight at 4° C. Each reaction mix was purified by Sephadex G-25 gel filtration (PD-10 column, GE Healthcare Life Sciences) equilibrated with PBS, pH 7.4. Protein-containing fractions were identified with Bradford reagent on parafilm, and pooled. The conjugate solution was dialysed in a Slide-A-Lyzer Dialysis cassette (Thermo Scientific, 20.000 MWCO) against PBS, pH 7.4, at 4° C. overnight. Protein concentration was determined by use of RotiQuant-Assay (Carl Roth, Germany). Conjugate solutions were adjusted to protein concentrations of 5 mg/ml (~$3.44\times10^{-5}$M), sterile filtered and stored at 4° C. Conjugates were designated as "T-D265C-30.2669", "T-D265C-30.2670", "T-D265C 30.2671", "T-D265C-30.2672", and "T-D265C-30.2684".

In Coomassie staining under reducing conditions the light and heavy chain of the amatoxin antibody conjugates and the naked antibody had the expected apparent mass of app. 25 and 50 kDa. In case of the amatoxin antibody conjugates an up-shift of the protein signal of the heavy chain was observed, compared to the naked antibody, indicating toxin-conjugation to the heavy chain. In anti-Amanitin Western Blots under reducing conditions the thiomab conjugates showed a signal for the heavy chain at app. 55 kDa and no signal for the light chain. This indicated toxin conjugation exclusively at the heavy chain.

Example 34: Cytotoxicity Studies on HER2-Positive Tumor Cell Lines In Vitro

Cytotoxic activity of Trastuzumab (Anti-Her2neu-specific antibody)-amatoxin conjugates was evaluated in vitro on HER2-positive tumor cell lines SKBR-3 (breast cancer), NCI-N87 (gastric cancer), and JIMT-1 (breast cancer) using a chemiluminescent BrdU-ELISA incorporation assay (Roche). The conjugates tested were comprising one conjugate with an aromatic cyclic acetal with a dipeptidic cleavage site according to the present invention linked to aa3 of amatoxin (T-D265C-30.2684), one conjugate with a para-amino-benzylether linker with a dipeptidic cleavage site linked to aa4 of amatoxin (T-D265C-30.1699), and 4 conjugates with aromatic cyclic acetal with a poly-ethylene glycol (PEG) linker linked to aa3 of amatoxin (T-D265C-30.2669 with p-$PEG_3$ linker, -30.2670 with m-$PEG_3$ linker, -30.2671 with p-$PEG_3$ linker and aryl fluoride moiety, -30.2672 with o-$PEG_3$ linker and aryl-bromide moiety), respectively.

HDP 30.2684

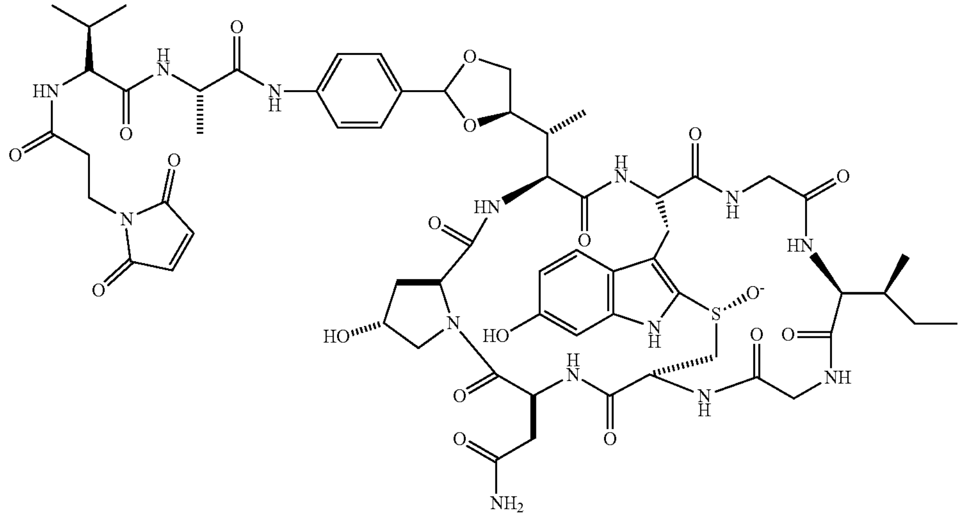

-continued
HDP 30.2669
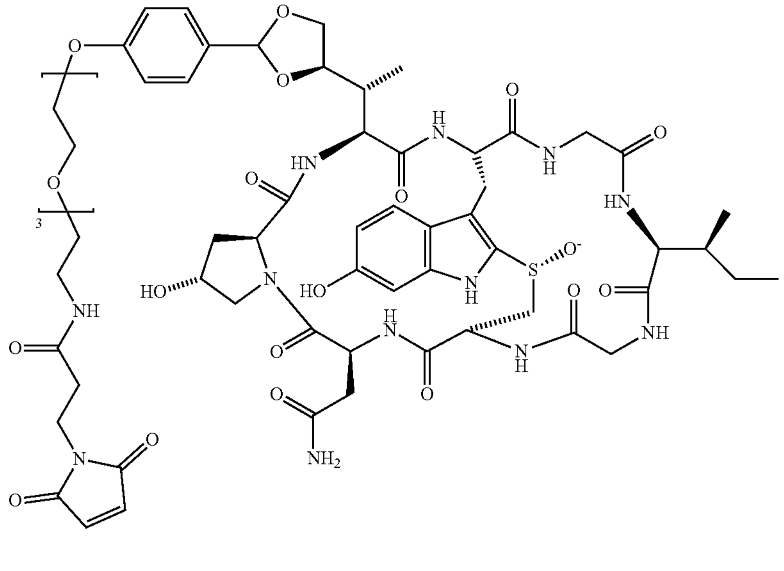
HDP 30.2670
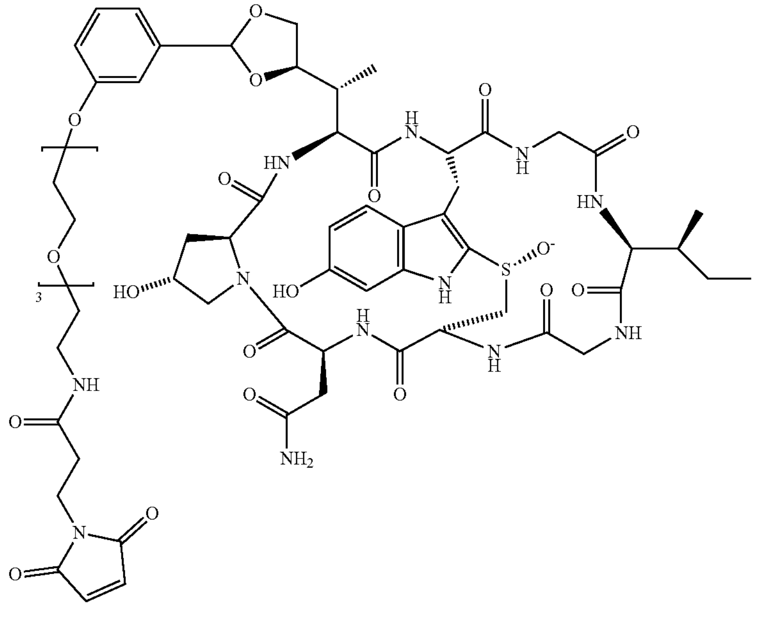

-continued
HDP 30.2671
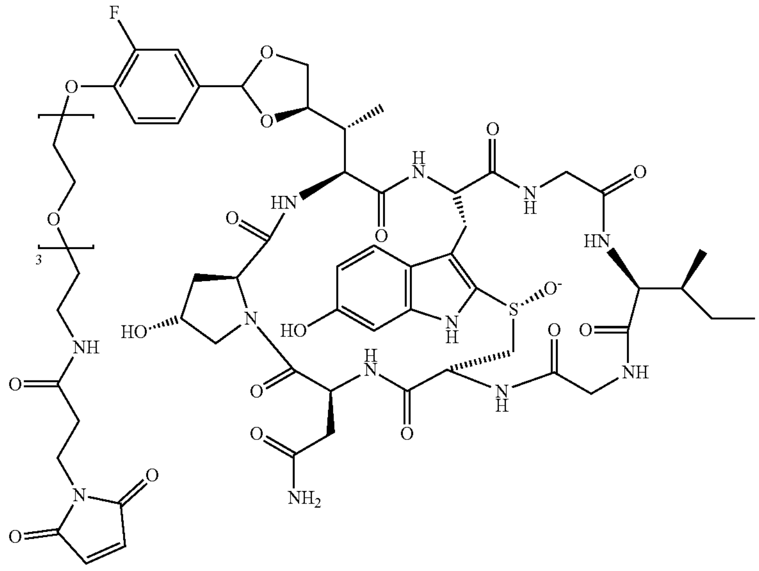
HDP 30.2672
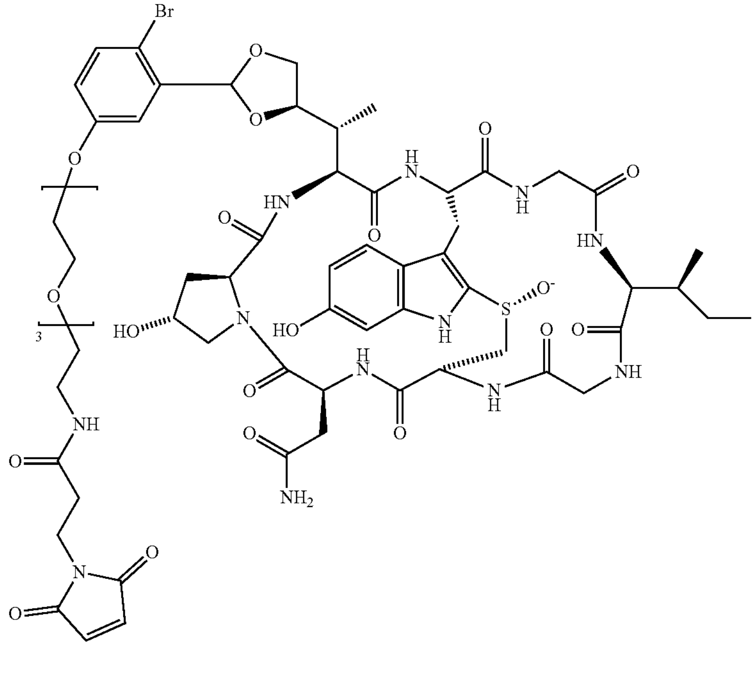

-continued

HDP 30.1699

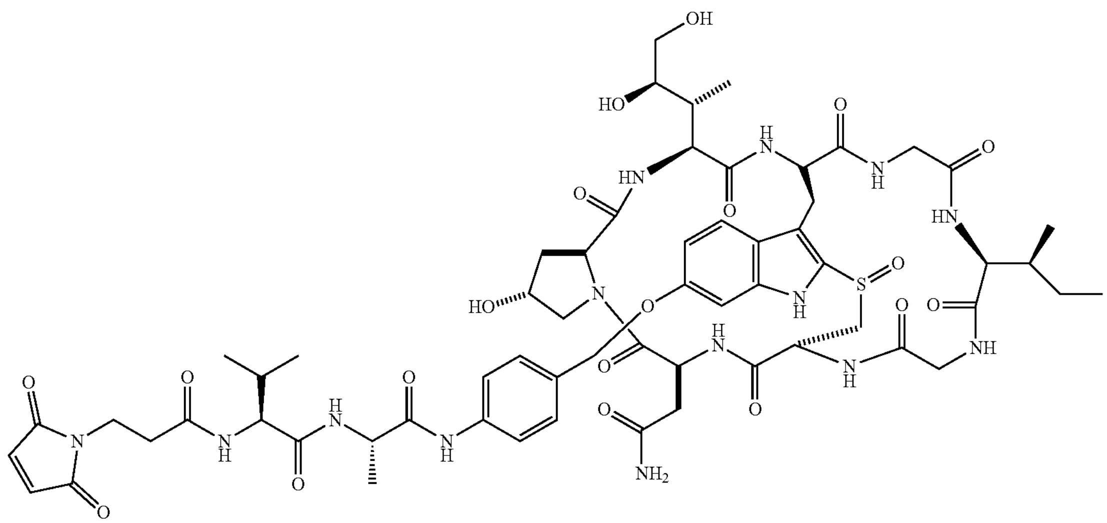

Figure 2:
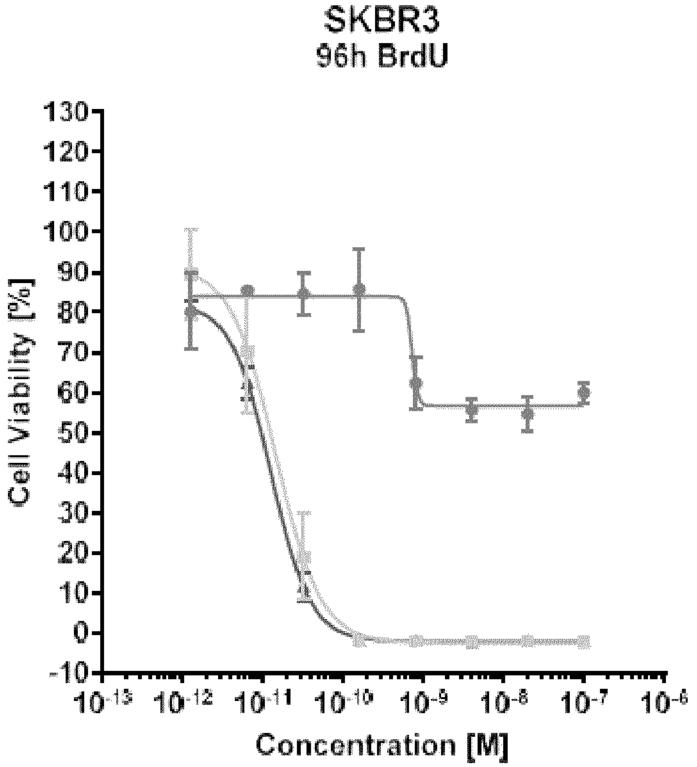
FIG. 2 Results of cytotoxicity studies on SKBR-3 cells in a BrdU assay after incubation at 96 hours FIG. 3 Results of cytotoxicity studies on NCI-N87 cells in a BrdU assay after incubation at 96 hours FIG. 4 Results of cytotoxicity studies on JIMT-1 cells in a BrdU assay after incubation at 96 hours FIG. 5 Results of the efficacy study of acetal linker conjugates in SKOV-3 xenograft tumor mouse models in vivo FIG. 6 Results of in vivo tolerability study of conjugates T-D265C-30.2669 and T-D265C-30.2684 in NOD/SCID mice in vivo Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.
Figure 3:
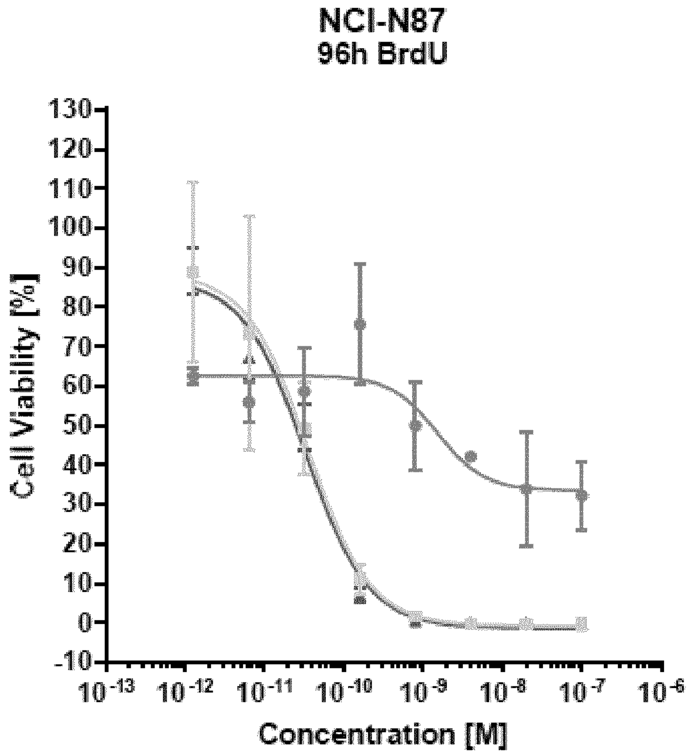
Figure 4:
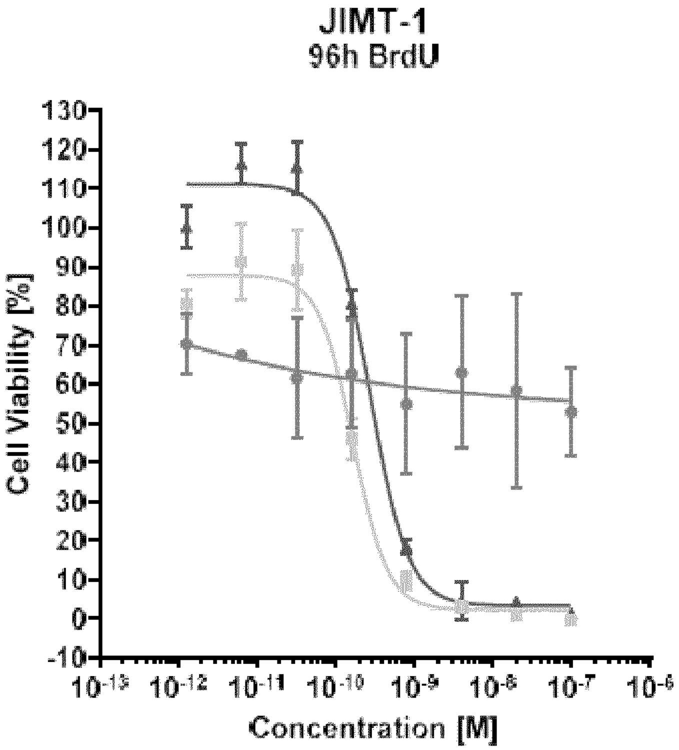

Results of cytotoxicity studies on SKBR-3 cells are shown in FIG. 2, results of cytotoxicity studies on NCI-N87 cells are shown in FIG. 3, and the results on JIMT-1 cells are shown in FIG. 4.

$EC_{50}$ values of the various Trastuzumab-amatoxin conjugates on different Her2-positive cell lines are shown in Table 1:

| | EC 50 [M] | | |
|---|---|---|---|
| T-D265C | SKBR-3 | NCI-N87 | JIMT-1 |
| PEG 30.2669 | $5.61 \times 10^{-11}$ | $1.32 \times 10^{-09}$ | — |
| PEG 30.2670 | $6.89 \times 10^{-10}$ | $1.67 \times 10^{-09}$ | — |
| PEG 30.2671 | $5.08 \times 10^{-10}$ | $9.7 \times 10^{-10}$ | — |
| PEG 30.2672 | $(7.19 \times 10^{-10})$ | $(1.52 \times 10^{-09})$ | — |
| V-A 30.2684 | $1.44 \times 10^{-11}$ | $3.56 \times 10^{-11}$ | $1.69 \times 10^{-10}$ |
| V-A 30.1699 | $1.25 \times 10^{-11}$ | $3.31 \times 10^{-11}$ | $2.77 \times 10^{-10}$ |

[( ), >50% cell viability; —, no cytotoxicity; V-A, valin-alanin dipeptide; PEG, poly ethylene glycol]

The cytotoxicity of the conjugate T-D265C-30.2684 according to the present invention was comparable to the cytotoxicity of the conjugate T-D265C-30.1699. The cytotoxicity of the conjugate T-D265C-30.2684 according to the present invention was slightly higher on SKBR-3 cells, but considerably higher on NCI-N87 cells and JIMT-1 cells, when compared to the conjugate T-D265C-30.2669 comprising an aromatic cyclic acetal with a PEG linker.

The ADCs T-D265C-30.2684 and T-D265C-30.1699, both having cleavable Val-Ala linkers, showed full-blown cytotoxic potential on the cell lines tested. The acid-labile ADCs T-D265C-30.2670, T-D265C-30.2671 and T-D265C-30.2672 showed only growth inhibition with residual cell viabilities of app. 65%, 50% and 60%, respectively, on SKBR-3 cells, and no cytotoxicity at all on JIMT-1 cells.

The amatoxin derivative HDP 30.2684 is as effective as HDP 30.1699 in vitro, but is synthesized much faster. During synthesis of HDP 30.1699 three HPLC purifications are necessary, whereas the synthesis of HDP 30.2684 takes only one.

Example 35: Efficacy of Acetal Linker Conjugates in a SKOV-3 Xenograft Tumor Mouse Model In Vivo The study consisted of 7 experimental groups with 10 female NOD Scid mice each bearing subcutaneous Her2-positive SKOV-3 (human ovary) tumors. The efficacy of two aromatic cyclic acetal conjugates (T-D265C-30.2684, T-D265C-30.2669) with amatoxin aa3-linkage in escalating doses was compared to T-D265C-30.1699, having a para-amino-benzylic linker with a dipeptidic cleavage site linked to aa4 of amatoxin, and untreated control. Mice were treated with single dose i.v.

The experimental setup is shown in Table 2:

| Group | Compound | *dose protein [mg/kg] | *dose amanitin [μg/kg] | Route | Schedule | Animals (n) |
|---|---|---|---|---|---|---|
| 1 | PBS (Control) | 10 mL/kg | — | i.V. | Single dose | 10 |
| 2 | T-D265C-30.2669 | 2.0 | 37.10 | i.v. | Single dose | 10 |
| 3 | T-D265C-30.2669 | 6.0 | 111.29 | i.V. | Single dose | 10 |
| 4 | T-D265C-30.2684 | 2.0 | 36.93 | i.v. | Single dose | 10 |
| 5 | T-D265C-30.2684 | 6.0 | 110.80 | i.v. | Single dose | 10 |
| 6 | T-D265C-30.1699 | 1.0 | tbd* | i.v. | Single dose | 10 |
| 7 | T-D265C-30.1699 | 2.0 | tbd* | i.v. | Single dose | 10 |

Figure 5:
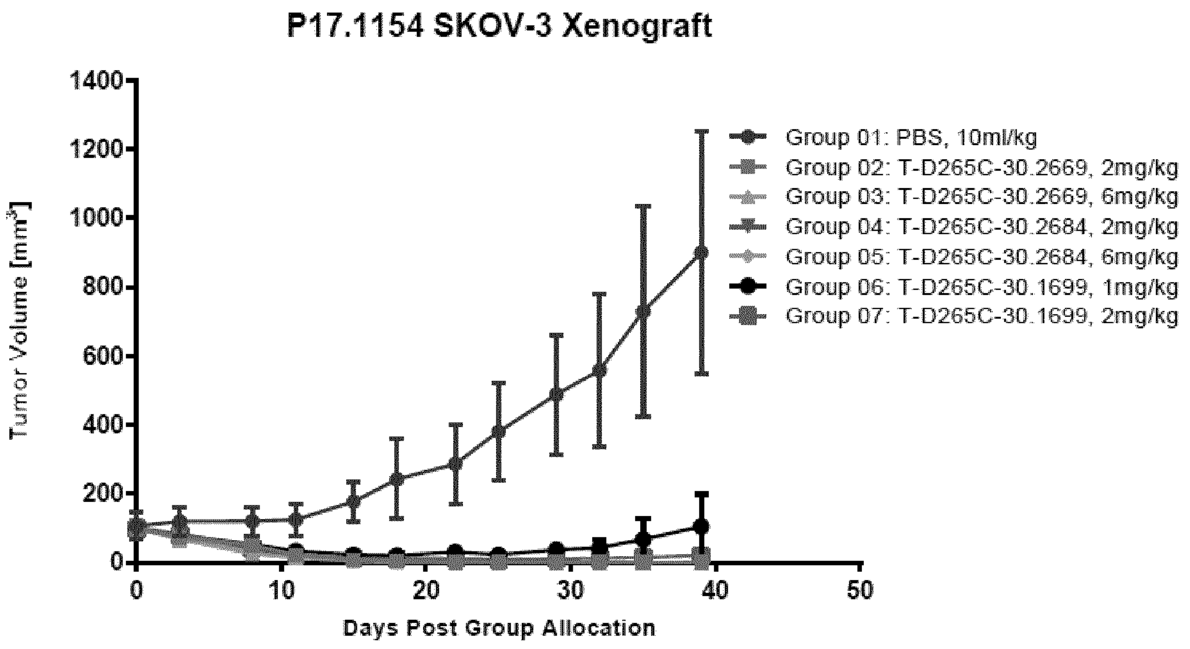

Results of the study are shown in FIG. 5.

All animals were tumor-free in groups treated with cyclic acetal amatoxin-drug conjugates. No tumor free animals were obtained in the animal group treated with 1 mg/kg T-D265C-30.1699. 4 out of 10 animals were tumor free in the animal group treated with 2 mg/kg T-D265C-30.1699.

Example 36: Tolerability of Acetal Linker Conjugates in an In Vivo Mouse Model

The tolerability of amatoxin ADCs T-D265C-30.2669 and T-D265C-30.2684, respectively, was evaluated in NOD/

Figure 6:
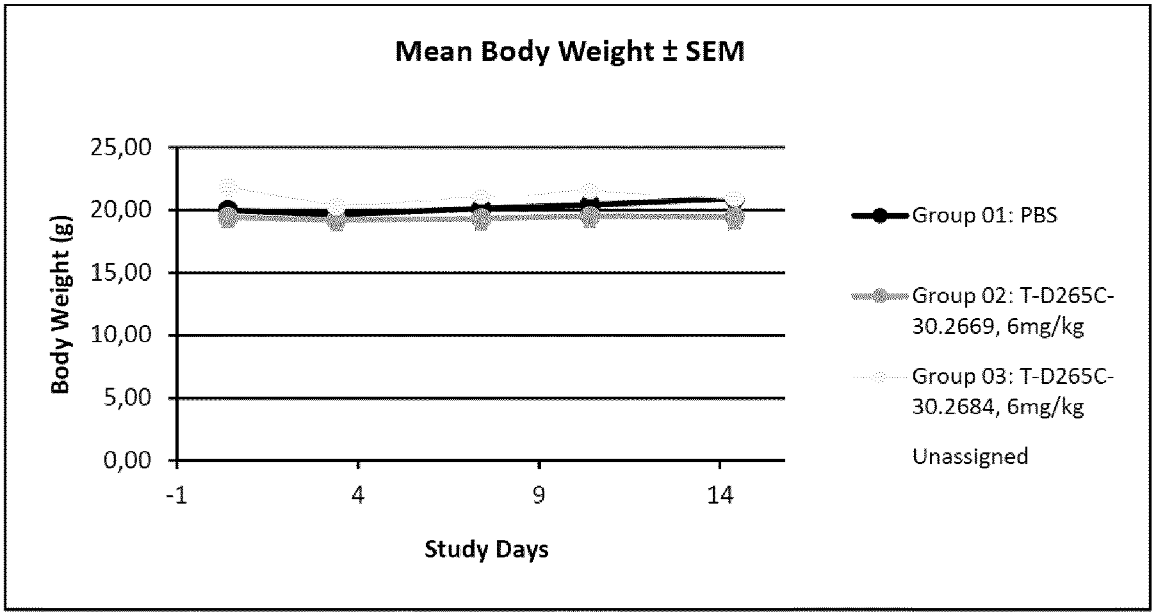

SCID mice after a single intravenous application. In total 21 animals were used. T-D265C-30.2669 and T-D265C-30.2684 were well tolerated at effective doses up to 6 mg/kg. The results are shown in FIG. 6.

REFERENCES

Binz H. K. et al. (2005). Engineering novel binding proteins from non-immunoglobulin domains. Nat. Biotechnol. Vol. 10: 1257-1268.

Chalouni C. and Doll S. (2018). Fate of Antibody-Drug Conjugates in Cancer Cells. Journal of Experimental & Clinical Cancer Research. Vol. 37: 20.

Gillies E. R. et al. (2004). Acetals as pH-Sensitive Linkages for Drug Delivery. Bioconjugate Chem. Vol. 15: 1254-1263.

Jeffrey et al. (2005). Design, Synthesis, and in Vitro Evaluation of Dipeptide-Based Antibody Minor Groove Binder Conjugates. J. Med. Chem. Vol. 48: 1344-1358.

Jeffrey et al. (2006). Development and Properties of β-Glucuronide Linkers for Monoclonal Antibody-Drug Conjugates. Bioconjugate Chem. Vol. 17: 831-840.

Poljak R. J. (1994). Production and structure of diabodies. Structure Vol. 2: 1121-1123.

Tranoy-Opalinski et al. (2014). β-Glucuronidase-responsive prodrugs for selective cancer chemotherapy: An update. European Journal of Medicinal Chemistry Vol. 74: 302-313.

Wang et al. (2019). Three decades of nucleic acid aptamer technologies: Lessons learned, progress and opportunities on aptamer development. Biotechnology Advances Vol. 37: 28-50.

Wieland T. and Faulstich H. (1978). Amatoxins, Phallotoxins, Phallolysin, and Antamanide: The biologically active components of poisonous *Amanita* mushrooms. CRC Crit Rev Biochem. Vol. 5(3): 185-260.

What is claimed is:

1. A compound of Formula I or II comprising a cytotoxic drug moiety

I

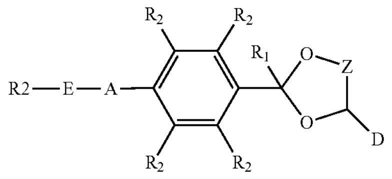

II

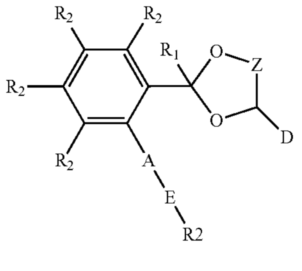

wherein

D is a cytotoxic drug moiety comprising at least one 1,2- or 1,3-diol moiety upon release from the compound, wherein D is an amatoxin selected from the group consisting of α-amanitin, β-amanitin, amanin, amaninamide, analogues thereof, derivatives thereof, and salts thereof;

Z is $CH_2$, $CH_2$—$CH_2$ or CHR3-CHR3, wherein each R3 is independently H or an alkyl group, optionally substituted by one or more heteroatoms;

R1 is H or a $C_1$-$C_6$ alkyl group;

A is an electron donating group;

E is a cleavage site; and each R2 is independently H, an electron withdrawing group, or an electron donating group.

2. The compound according to claim 1, wherein the electron donating group A is selected from O, NH, and S.

3. The compound according to claim 1, wherein the cleavage site E is an enzymatically cleavable moiety comprising two or more amino acids.

4. A conjugate comprising the compound according to claim 1 and a T-L moiety, wherein said T-L moiety is substituting at least one of residues R2 in Formula I or II, and wherein L is a linker and T is a target binding moiety.

5. The conjugate according to claim 4, wherein the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

6. The conjugate according to claim 4, wherein the linker L comprises a moiety selected from at least one of the following moieties: a disulfide, an ether, a thioether, an amine, an ester, a carboxamide, a urethane, and a urea moiety.

7. The conjugate according to claim 4, wherein the target binding moiety T is selected from the group consisting of (i) an antibody or antigen-binding fragment thereof;

(ii) an antibody-like protein, and (iii) a nucleic acid aptamer.

8. The conjugate according to claim 7, wherein the antibody or the antigen-binding fragment thereof is a diabody, a tetrabody, a nanobody, a chimeric antibody, a deimmunized antibody, a humanized antibody, or a human antibody.

9. The conjugate according to claim 7, wherein the antigen binding fragment is selected from the group consisting of Fab, F(ab')2, Fd Fv, single-chain Fv, and disulfide-linked Fvs (dsFv).

10. The conjugate according to claim 4, having Formula I or IV

III

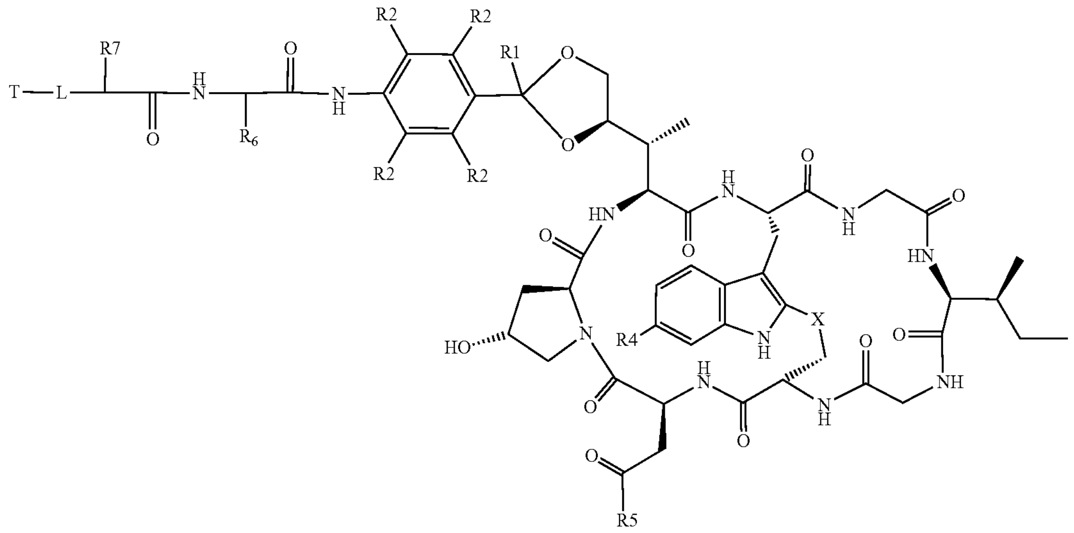

IV

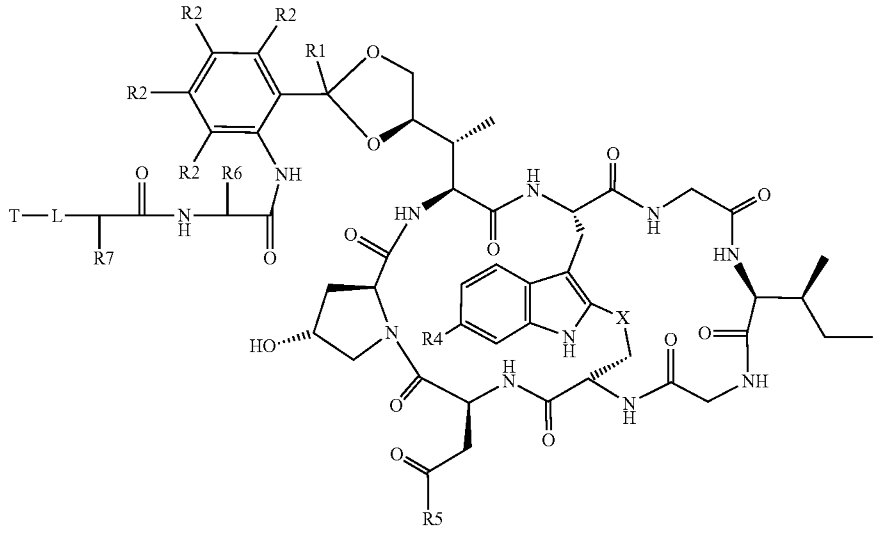

wherein

X is S, SO, or $SO_2$;

R1 is H or a $C_1$-$C_6$ alkyl group;

each R2 is independently H, an electron withdrawing group, or an electron donating group;

R4 is H, OH, O—$C_1$-$C_8$-alkyl, $NO_2$, $NH_2$, F, Cl, Br, or SH;

R5 is OH, $NH_2$, or NHOH;

R6 and R7 independently are side chains of natural or unnatural amino acids;

L is a linker, and

T is a target binding moiety.

11. The conjugate according to claim 4, having Formula V

V

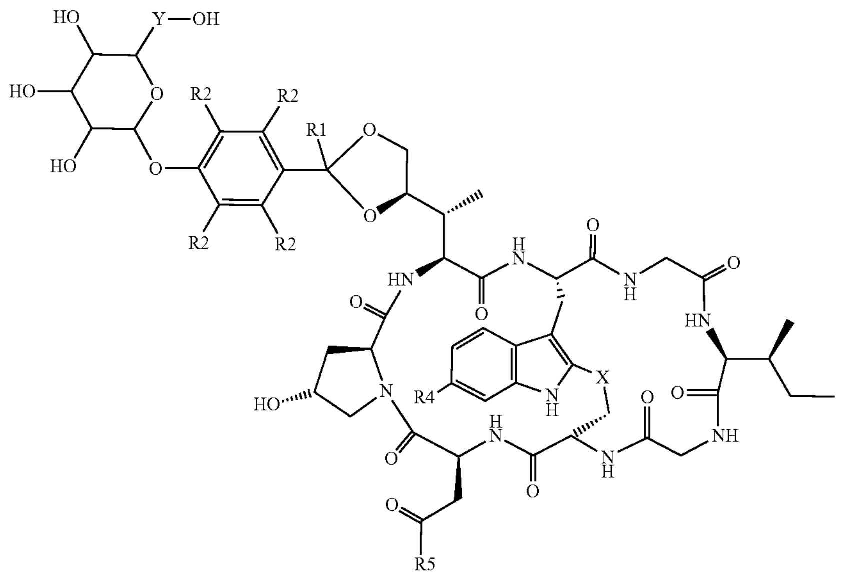

wherein

X is S, so, or $SO_2$;

Y is $CH_2$ or CO;

R1 is H or a $C_1$-$C_6$ alkyl group;

each R2 is independently H, an electron withdrawing group, or an electron donating group, wherein at least one R2 group is substituted by said T-L moiety;

R4 is H, OH, O—$C_1$-$C_8$-alkyl, $NO_2$, $NH_2$, F, Cl, Br, or SH;

R5 is OH, $NH_2$, or NHOH;

L is a linker, and

T is a target binding moiety.

12. The conjugate according to claim 4, having Formula VI

VI

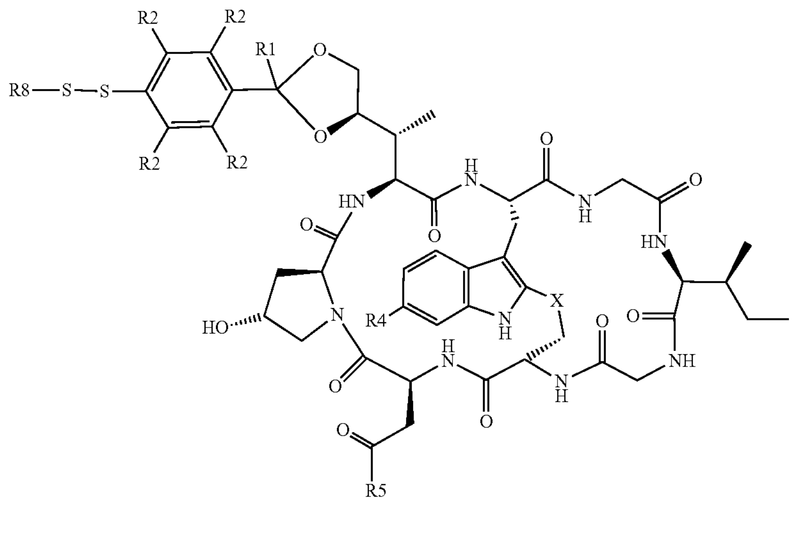

wherein

X is S, SO, or $SO_2$;

R1 is H or a $C_1$-$C_6$ alkyl group;

each R2 is independently H, an electron withdrawing group, or an electron donating group, except one R2 is substituted by said T-L-moiety, if R8 is not a T-L-moiety;

R4 is H, OH, O—$C_1$-$C_8$-alkyl, $NO_2$, $NH_2$, F, Cl, Br, or SH;

R5 is OH, $NH_2$, or NHOH;

R8 is a linear or branched alkyl group or, if no R2 is a T-L-moiety, is a T-L-moiety;

L is a linker, and

T is a target binding moiety.

13. The conjugate according to claim 4, having Formula VII

VII

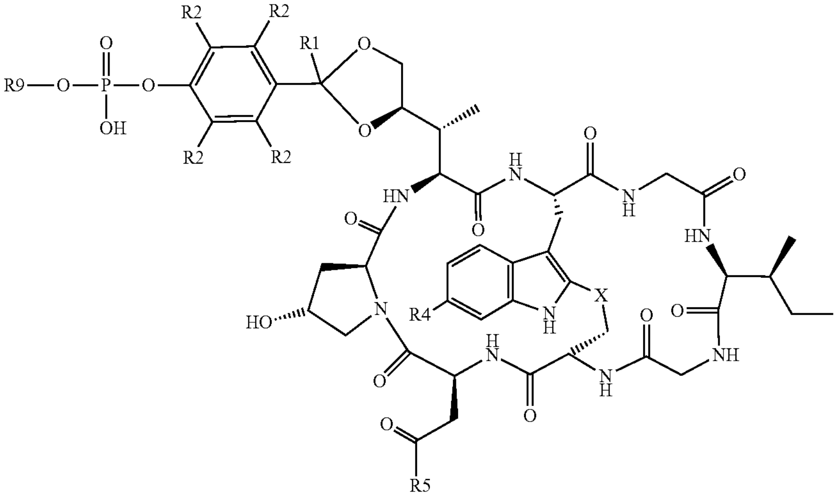

wherein

X is S, SO, or $SO_2$;

R1 is H or a $C_1$-$C_6$ alkyl group;

each R2 is independently H, an electron withdrawing group, or an electron donating group, except one R2 is substituted by said T-L-moiety, if R9 is not a T-L-moiety;

R4 is H, OH, O—$C_1$-$C_8$-alkyl, $NO_2$, $NH_2$, F, Cl, Br, or SH;

R5 is OH, $NH_2$, or NHOH;

R9 is H or a linear or branched alkyl group or, if no R2 is a T-L-moiety, is a T-L-moiety;

L is a linker, and

T is a target binding moiety.

14. The conjugate according to claim 4, represented by Formula VIII

VIII

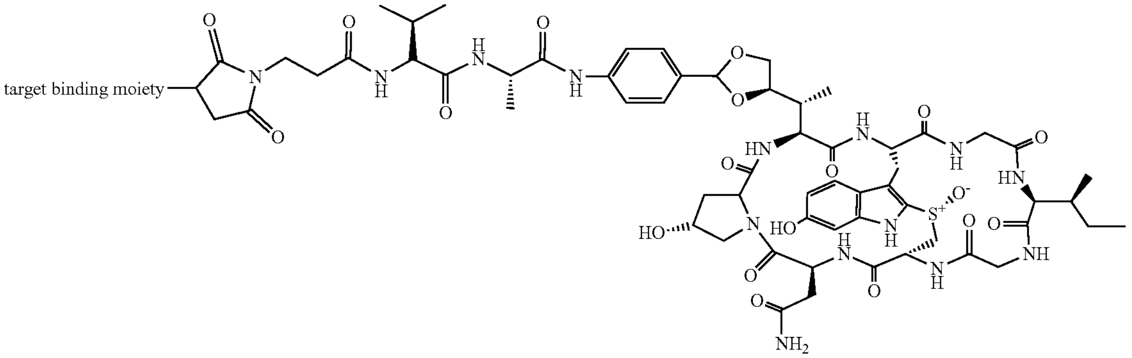

or Formula IX

IX

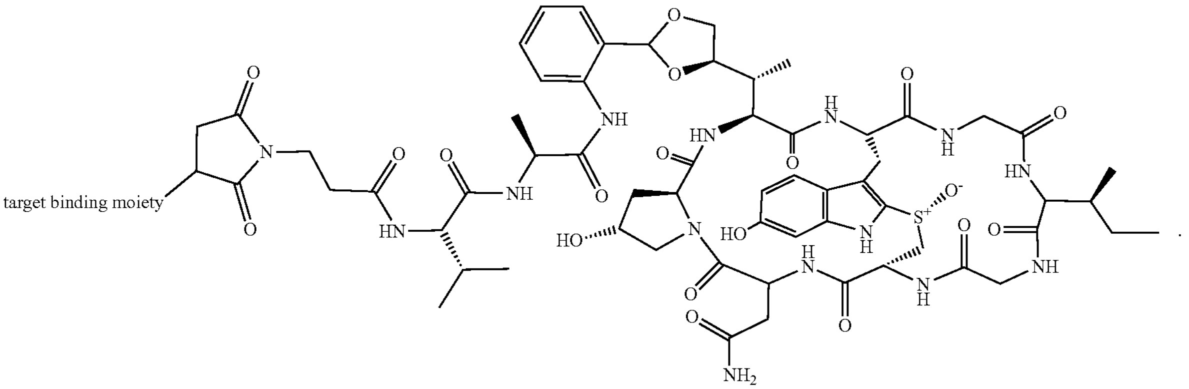

15. A method for synthesizing the conjugate according to claim 4 by reacting a 1,2- or 1,3-diol with a dimethyl benzylidene acetal in an aprotic solvent under acidic conditions.

16. A method for synthesizing the conjugate according to claim 4 by reacting an amatoxin with a dimethyl benzylidene acetal in an aprotic solvent under acidic conditions.

17. The method according to claim 6, wherein the amatoxin is selected from alpha-amanitin, beta-amanitin, amanine, amaninamide, and their respective thioethers.

18. The method according to claim 16, wherein the aprotic solvent is DMF and/or the acid is trifluoroacetic acid.

19. A pharmaceutical composition comprising the conjugate according to claim 4 and one or more pharmaceutically acceptable diluents, carriers, excipients, fillers, binders, lubricants, disintegrants, adsorbents, and/or preservatives.

20. A method of treating cancer in a patient, wherein the method comprises systemic administration of a conjugate according to claim 4 or a pharmaceutical composition thereof.

21. The method of treating cancer in a patient according to claim 20, wherein the cancer is selected from the group consisting of breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

22. A compound of Formula I or II comprising a cytotoxic drug moiety

I

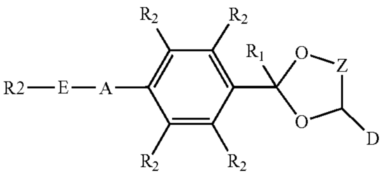

-continued

II

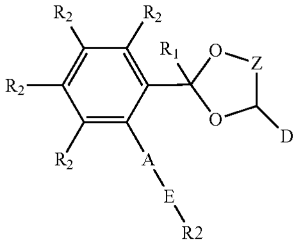

wherein

D is a cytotoxic drug moiety comprising at least one 1,2- or 1,3-diol moiety upon release from the compound, wherein D is an amatoxin selected from the group consisting of α-amanitin, β-amanitin, amanin, amaninamide, and salts thereof;

Z is $CH_2$, $CH_2$—$CH_2$ or CHR3-CHR3, wherein each R3 is independently H or an alkyl group, optionally substituted by one or more heteroatoms;

R1 is H or a $C_1$-$C_6$ alkyl group;

A is an electron donating group;

E is a cleavage site; and each R2 is independently H, an electron withdrawing group, or an electron donating group.

* * * * *